(12) United States Patent
Gilmore et al.

(10) Patent No.: US 11,731,101 B2
(45) Date of Patent: Aug. 22, 2023

(54) MODULAR CONTINUOUS FLOW DEVICE

(71) Applicant: Max-Planck-Gesellschaft zur Forderung der Wissenschaften e.V., Munich (DE)

(72) Inventors: Kerry Gilmore, Berlin (DE); Peter H. Seeberger, Kleinmachnow (DE); Bartholomaus Pieber, Potsdam (DE); Sourav Chatterjee, Potsdam (DE)

(73) Assignee: MAX-PLANCK-GESELLSCHAFT ZUR FORDERUNG DER WISSENSCHAFTEN E.V., Munich (DE)

( * ) Notice: Subject to any disclaimer, the term of this patent is extended or adjusted under 35 U.S.C. 154(b) by 1250 days.

(21) Appl. No.: 16/080,708

(22) PCT Filed: Feb. 27, 2017

(86) PCT No.: PCT/EP2017/054536
§ 371 (c)(1),
(2) Date: Aug. 29, 2018

(87) PCT Pub. No.: WO2017/148874
PCT Pub. Date: Sep. 8, 2017

(65) Prior Publication Data
US 2021/0187468 A1    Jun. 24, 2021

(30) Foreign Application Priority Data
Feb. 29, 2016 (EP) ..................... 16157958

(51) Int. Cl.
*B01J 19/00* (2006.01)
*B01J 19/12* (2006.01)
(Continued)

(52) U.S. Cl.
CPC ......... *B01J 19/0046* (2013.01); *B01J 19/126* (2013.01); *B01J 2219/00033* (2013.01);
(Continued)

(58) Field of Classification Search
CPC ........ B01J 19/00; B01J 19/0046; B01J 19/08; B01J 19/12; B01J 19/122; B01J 19/126;
(Continued)

(56) References Cited

U.S. PATENT DOCUMENTS 6,994,827 B2 * 2/2006 Safir .................... B01J 19/0046
422/135
8,355,625 B2 * 1/2013 Erasmus ................. F24H 1/202
392/445

(Continued)

OTHER PUBLICATIONS

International Search Report and Written Opinion for International Patent Application No. PCT/EP2017/054536 dated May 29, 2017, 2 pages.

*Primary Examiner* — Natasha E Young
(74) *Attorney, Agent, or Firm* — Amin, Turocy & Watson, LLP

(57) ABSTRACT

The invention refers to a modular continuous flow device for automated chemical multistep synthesis under continuous flow conditions. The device comprises a plurality of different types of continuous flow modules and a valve assembly for connecting the continuous flow modules to each other in a parallel or radial manner. This arrangement allows conducting chemical reaction sequences by pre-synthesizing and intermediately storing or simultaneously synthesizing at least one intermediate product which is needed in the main synthetic reaction sequence in order to obtain the final product.

12 Claims, 9 Drawing Sheets

(51) Int. Cl.
  *C07C 255/23* (2006.01)
  *C07D 249/04* (2006.01)
  *C07D 321/10* (2006.01)

(52) U.S. Cl.
  CPC ............... *B01J 2219/0072* (2013.01); *B01J 2219/00281* (2013.01); *B01J 2219/00394* (2013.01); *B01J 2219/00418* (2013.01); *B01J 2219/00479* (2013.01); *B01J 2219/00585* (2013.01); *C07C 255/23* (2013.01); *C07D 249/04* (2013.01); *C07D 321/10* (2013.01)

(58) Field of Classification Search
  CPC .......... B01J 2219/00; B01J 2219/00002; B01J 2219/00027; B01J 2219/00033; B01J 2219/00274; B01J 2219/00277; B01J 2219/00279; B01J 2219/00284; B01J 2219/00351; B01J 2219/00389; B01J 2219/00391; B01J 2219/00394; B01J 2219/00418; B01J 2219/00479; B01J 2219/00583; B01J 2219/00585; B01J 2219/00718; B01J 2219/0072; C07C 255/00; C07C 255/01; C07C 255/23; C07D 321/00; C07D 321/02; C07D 321/10; C07D 249/00; C07D 249/02; C07D 249/04

See application file for complete search history.

(56) References Cited

U.S. PATENT DOCUMENTS

| | | |
|---|---|---|
| 2002/0048536 A1* | 4/2002 | Bergh ................. B01J 4/00 422/130 |
| 2003/0156989 A1 | 8/2003 | Safir et al. |
| 2010/0183482 A1 | 7/2010 | Lohf |
| 2012/0076692 A1* | 3/2012 | Miraghaie ........... B01J 19/0093 422/49 |

* cited by examiner

Figure 1 – State of the art a)

b)

Figure 3
a)
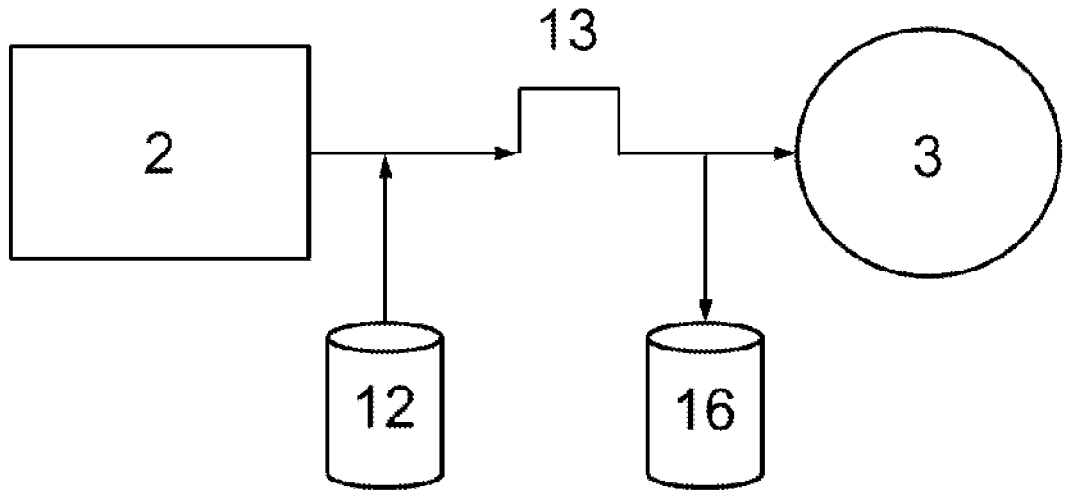
b)
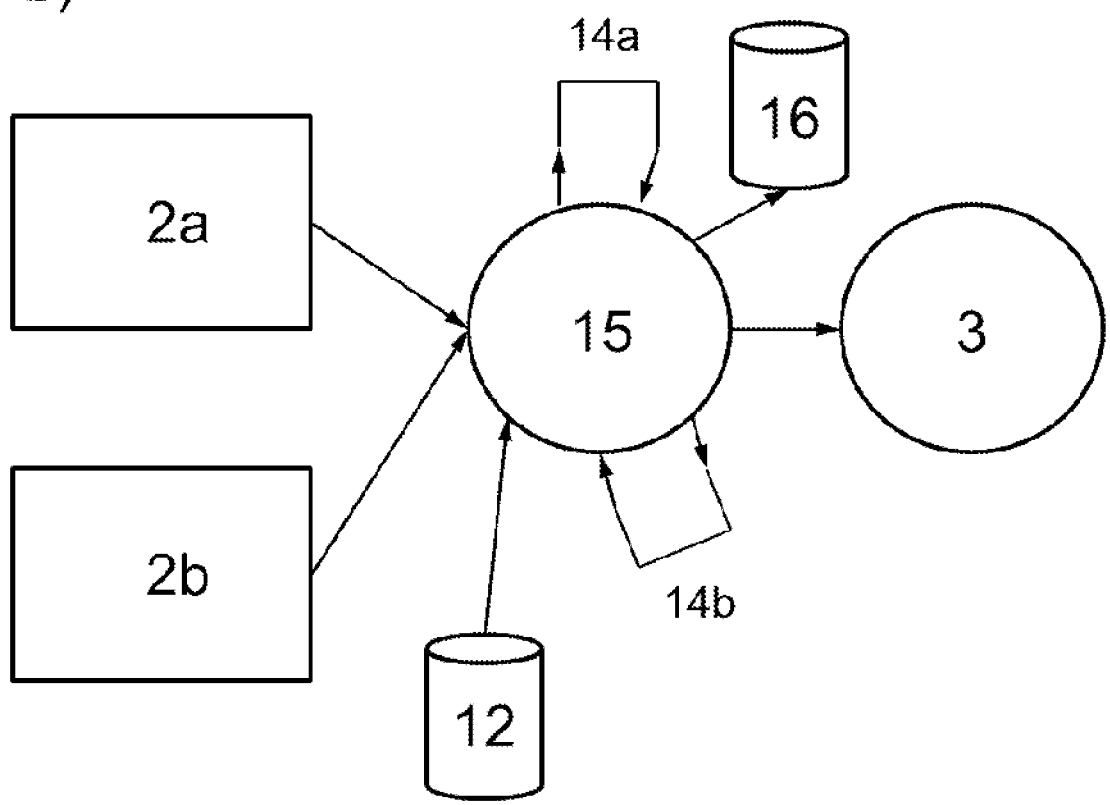

MODULAR CONTINUOUS FLOW DEVICE

This application is a national stage application claiming priority to PCT/EP2017/054536, now WO 2017/148874, filed Feb. 27, 2017, which claims priority to European Patent Application Serial No. EP16157958.6, filed on Feb. 29, 2016.

The invention refers to a modular continuous flow device for automated chemical multistep synthesis under continuous flow conditions. The device comprises a plurality of different types of continuous flow modules and a valve assembly for connecting the continuous flow modules to each other in a parallel or radial manner. This arrangement allows conducting chemical reaction sequences by pre-synthesizing and intermediately storing or simultaneously synthesizing at least one intermediate product which is needed in the main synthetic reaction sequence in order to obtain the final product.

BACKGROUND OF THE INVENTION

Within the increasing number of available chemical transformations and the resulting access to new target compounds and classes, the demand for new target structures with new desirable properties is also rising. Automated chemical systems allow for the rapid and parallel production of compounds. They can be operated unattended which keeps the costs for skilled laboratory worker and also the risk of being exposed to toxic substances on a minimum.

Automated chemical systems are well known in the prior art, but are mostly limited to a specific type of reaction or reaction sequence. For instance highly-efficient automated solid phase synthesizers for peptides or oligonucleotides employ solid support bounded substrates which are brought to reaction iteratively in a specific order of limited steps like activation/coupling/deprotection under a restricted set of conditions.

Further these synthesizers can only perform linear syntheses, where the desired target compound is constructed stepwise from a single starting material. More efficient than a linear synthesis is a convergent synthesis, where individual precursors or intermediates are synthesized and then combined to form a new intermediate or the final target compound. However, convergent synthesis requires storing intermediates during a multistep synthesis and running reactions parallel. In contrast, many target compounds share similar core structures that can be utilized to construct libraries of compounds from common advanced intermediates by divergent synthesis.

It would be desirable to provide a single synthesizer that can perform linear, convergent and divergent syntheses.

Burke et al. (Science 2015, 347, 1221-1226) teach a "synthesis machine" that is able to couple a variety of aryl or alkyl halides with protected boronic acids sequentially to a variety of small molecules. The synthesizer is limited to only one iterative set of reaction steps, i.e. deprotection, coupling and purification that can be repeated several times for multi-step syntheses.

Ghislieri et al. (Angew. Chem. Int. Ed. 2015, 54, 678-682) and Nobuta/Xiao et al. (Chem. Commun., 2015, 51, 15133-15136) disclose a Chemical Assembly System (CAS) that combines flow reactor modules in an interchangeable fashion for divergent or convergent multistep syntheses under continuous flow conditions. A variety of small molecules are obtained by changing the starting material, choosing different reagents and by changing the order of flow reactor modules. Every reaction step a separate reactor module. Thus no reactor module can be used repeatedly in a multistep synthesis. This system is limited to a small number of reactor modules due to practicality reasons and emerging dispersion issues. The system is further limited to reagents that require the same conditions for these transformations.

Schwalbe et al. disclose in the European patent EP 1 174 184 B1 an automated chemical processing system including a stacked plate reactor as reaction module. Reactions can be run under continuous flow conditions. The arrangement of the reaction modules is linear and fixed. Every reaction step in a multistep synthesis requires a separate reaction module. Reassembling of the system is necessary, when another multistep synthesis is conducted. The disclosed stacked plate reactor is limited to specific reaction conditions, mainly elevated temperatures.

Commercial automated flow reactor systems are already available. They can be purchased for instance from Vapourtec Ltd. or Syrris Ltd. However these systems are very limited with respect to the reagent supply. Only up to 6 different reagents can be delivered which restricts the number of possible reactions and the number of steps that can be performed. For performing more than two consecutive steps multiple systems must be used.

The US patent application US 2003/156959 A1 discloses semi-continuous or continuous reactors in a parallel arrangement, wherein each reactor is in fluid communication with one feed distribution valve providing reagents from a reagent source vessel. A reagent is pumped from the reagent source vessel to the feed distribution valve which selectively provides the reagents to each reactor. The reactors are small volume reaction vessels and integral with a reactor block. The reaction mixture is removed from each reactor by a discharge line to a waste reservoir, a sampling system for analytics or to another reaction system. This system is not capable of performing multistep syntheses since a refeeding of the reaction products into the feed distribution valve is not possible.

The German patent D02 DE 10 2007 028116 B3 discloses a microfluidic system for mixing of at least two starting materials in similar reaction channels under continuous flow conditions, wherein the reaction channels are in a parallel arrangement. The valve assemblies are in connection to four syringe pumps and allow fluid communication between each starting material and each reaction or mixing channel via a distribution line in such a way that the flow rate of the starting materials remains constant. Each valve has three positions: for filling the syringe pumps, for applying a predefined pressure to the filled syringe pumps and for distributing the starting material to the reaction or mixing channels via the distribution lines. This system is also not capable of performing multistep syntheses since once the stream has passed the reaction or mixing channels a refeeding to the valve assembly is not possible.

Seeberger et al. (WO2013030247A1) teach a method and a continuous flow reactor for the continuous preparation of the anti-malaria drug artemisinin from dihydroartemisinic acid. Three reactions for the conversion of dihydroartemisinic acid to artemisinin are run in a single continuous flow reactor: the photooxidation of dihydroartemisinic acid with singlet oxygen, the acid-mediated cleavage and the oxidation with triplet oxygen to artemisinin. The continuous flow reactor allows easy scale-up, provides a large surface-to-volume ratio that ensures efficient irradiation and enables precise reaction control.

Kopetzki et al. (WO2015007693A1) disclose a method and a continuous flow reactor for the synthesis of dihydroartemisinin and artemisinin derivatives. Reduction of artemisinin to dihydroartemisinin requires a column reactor containing a special combination of a hydride reducing agent and at least one activator. Further reaction of dihydroartemisinin to artemether, arteether, artesunate, artelinic acid and several other artemisinin derivatives is achieved in a single continuous flow reactor.

Thus, the state of the art discloses continuous flow reactors for linear multiple step reactions performing a variety of different chemical reactions as well as purification procedures.

However further developed continuous flow reactors able to perform a convergent synthesis or able to run different reactions simultaneously are so far not known in the state of the art.

Accordingly, it would be desirable to provide a single versatile continuous flow device for automated multistep synthesis and especially for automated convergent multistep synthesis of a variety of small molecules by the same continuous flow device without rearranging or reconstructing the continuous flow device in order to adapt the continuous flow device to the next reaction sequence.

The objective of the present invention is solved by the teaching of the independent claims. Further advantageous features, aspects and details of the invention are evident from the dependent claims, the description, the figures, and the examples of the present application.

BRIEF DESCRIPTION OF THE INVENTION

The present invention relates to a modular continuous flow device for multistep synthesis comprising:
a) a plurality of continuous flow modules;
b) a reagent supply system;
c) a valve assembly;
d) means for controlling flow rates and/or pressure;
wherein each continuous flow module is connected to the valve assembly by at least one inlet and by at least one outlet; and
wherein the reagent supply system is connected to the valve assembly.

The continuous flow modules are reactors for performing a variety of chemical reactions such as a reactor for oxidizing a compound, reducing a compound, introducing a protecting group, deprotecting a compound, esterification, etherification, saponification, cyclisation, C—C-bond formation and the like. A continuous flow module can also be a reactor for intermediate product storage. The term "intermediate product storage" as used herein refers to an intermediate storage of an intermediate product synthesized by the modular continuous flow device of the present invention and that intermediate product will be used somewhere in the whole reaction procedure in order to synthesize the final product.

In accordance with the present invention the continuous flow modules are not directly connected to each other so that not a defined sequence of the modules is obtained like for a defined reaction sequence where the reaction starts in module 1, the reaction mixture is then transferred to module 2 for purification, then to module 3 for the second step, to module 4 for work-up, to module 5 for the third step and so on. The inventive modular continuous flow device provides the huge advantage to use any of the continuous flow modules first, any other one second, any further one third and so on, so that module 5 could be used first, thereafter module 4, then module 1, module 3 and lastly module 2. Any sequence of the continuous flow modules could be used in accordance with the present invention and also continuous flow modules could subsequently be used twice or several times due to the inventive connection of each continuous flow module to the valve assembly. Due to the connection of each continuous flow module to the valve assembly it is assured that the reaction mixture has to flow through the valve assembly after each reaction step, or each work-up step or each purification step, or each detection step which have to be performed in a specific continuous flow module, so that the reaction mixture can be transferred through the valve assembly to any of the other continuous flow modules. Thus, by means of the valve assembly any sequence of the continuous flow modules could be used. The only limitation is that the reaction mixture cannot be transferred into that continuous flow module from which it directly comes from. However, that does not mean that two reaction steps cannot be performed in the same continuous flow module. It is of course possible to perform in one continuous flow module one reaction step and after that step is performed without work-up or purification a further reaction step. A further limitation is that in case two reactions shall be performed simultaneously, each reaction has to be performed in one continuous flow module. It is of course not possible to perform two different reactions in one single continuous flow module. However the modular continuous flow device may of course comprise two a more similar continuous flow module, like a continuous flow module for photoreactions, so that the one reaction can be performed in the photoreactor 1 and the other reaction in the photoreactor 2.

The reaction mixture which is processed through the modular continuous flow device is most preferably liquid but could also be gaseous. The reagents added to the liquid or gaseous reaction mixture are most preferably solutions of the reagents or gaseous reagents like oxygen, but could also be solid reagents in powder form or pure liquid or viscous reagents.

Thus, the connection of these continuous flow modules is essential and allows the performance of two reaction steps in two different continuous flow modules simultaneously, because the continuous flow modules are not arranged in series like one continuous flow module after another but in parallel or radially so that any one of the continuous flow modules of the modular continuous flow device could be used as the first one, the second one, the last one or at any other position.

This makes the modular continuous flow device of the present invention flexible and adaptable without rearrangement of the device and without rearrangement of the continuous flow modules to various chemical reaction procedures and reaction sequences. Thus, the inventive modular continuous flow device is not an apparatus designed for carrying out one specific reaction procedure like the device for the synthesis of artemisinin as disclosed in WO2013030247A1, it is designed for performing a variety of different reaction sequences and chemical reactions in an arbitrary order.

Thus, the modular continuous flow device disclosed herein is not limited to a specific reaction procedure and is not limited to specific reaction conditions and is not limited to the synthesis of one specific final product.

Therefore, the present invention is directed to a modular continuous flow device for multistep synthesis comprising:
a) a plurality of continuous flow modules;
b) a reagent supply system;
c) a valve assembly;
d) means for controlling flow rates and/or pressure;

wherein the continuous flow modules do not have a direct connection to each other and are connected to each other only through the valve assembly; and wherein the continuous flow modules are also connected to the reagent supply system through the valve assembly.

This flexible arrangement of the continuous flow modules in series or radially is obtained by connecting each continuous flow module through a valve assembly to the other continuous flow modules, wherein each continuous flow module is connected to the valve assembly by at least one inlet and by at least one outlet (see FIG. 2a). This connection ensures that after performing one chemical step which could also be a purification step in one continuous flow module the reaction solution leaving this continuous flow module can be fed into any one of the other continuous flow modules present in the modular continuous flow device.

None of the state of the art continuous flow devices is able to provide such flexibility in performing a huge variety of chemical reaction sequences and in addition provides the opportunity to perform convergent reaction sequences, wherein synthesis of an intermediate product is required which is then used within a further reaction sequence during a defined reaction step.

DETAILED DESCRIPTION OF THE INVENTION

The invention concerns a device for carrying out multi-step syntheses under continuous flow conditions.

The present invention is directed to a modular continuous flow device for synthesis comprising:
a) a plurality of continuous flow modules;
b) a reagent supply system;
c) a valve assembly;
d) means for controlling flow rates and/or pressure;
wherein each continuous flow module is connected to the valve assembly by at least one inlet and by at least one outlet; and
wherein the reagent supply system is connected to the valve assembly and thereby to each continuous flow module.

Alternatively, the present invention is directed to a modular continuous flow device for multistep synthesis comprising:
a) a plurality of continuous flow modules;
b) a reagent supply system;
c) a valve assembly;
d) means for controlling flow rates and/or pressure;
wherein the continuous flow modules do not have a direct connection to each other and are connected to each other only through the valve assembly; and
wherein the continuous flow modules are not directly connected to the reagent supply system and are connected to the reagent supply system only through the valve assembly.

Essential to the modular continuous flow device of the present invention is that each continuous flow module is connected through at least one inlet and at least one outlet to the valve assembly. The continuous flow modules are not directly connected to each other. Depending on the valve position any connection between the continuous flow modules through the valve assembly can be established, thereby enabling for instance a serial or parallel connection.

In one embodiment of the present invention a parallel connection, also called herein parallel arrangement, is obtained by indirectly connecting all the continuous flow modules to each other through the valve assembly so that all continuous flow modules can be used in an arbitrary order.

Thus, the present invention is directed to a modular continuous flow device for multistep synthesis comprising:
a) a plurality of continuous flow modules in a parallel arrangement;
b) a reagent supply system;
c) a valve assembly;
d) means for controlling flow rates and/or pressure;
wherein each continuous flow module is connected to the valve assembly by at least one inlet and by at least one outlet and the reagent supply system is connected to the valve assembly.

Or in other words the present invention is directed to a modular continuous flow device for multistep synthesis comprising:
a) a plurality of continuous flow modules;
b) a reagent supply system;
c) a valve assembly;
d) means for controlling flow rates and/or pressure;
wherein each continuous flow module is connected to the valve assembly by at least one inlet and by at least one outlet and the reagent supply system is connected to the valve assembly and wherein the continuous flow modules are in a parallel arrangement.

Continuous Flow Modules

The continuous flow modules are flow reactors for performing a variety of different chemical reactions. The term "continuous flow modules" also comprises flow reactor(s) for purification and flow reactor(s) for intermediate product storage.

The term "a plurality of continuous flow modules" shall indicate that more than three and preferably 4, 5, 6, 7, or 8 continuous flow modules or even more than 8 continuous flow modules are present. However, all continuous flow modules are flow reactors and preferably none is a batch reactor. Thus, all reactions are carried out in a continuous manner. Moreover, most preferably all reactions are carried out under flow conditions, which means that the reaction mixture flows through the respective continuous flow module and the reaction is performed continuously until the complete reaction mixture has passed the respective continuous flow module or at least that part of the continuous flow module where the reaction takes place.

The continuous flow modules are, for example, reaction vessels, columns or just tubes wherein chemical reactions are performed and which are referred to herein as flow reactors for different purposes.

The continuous flow modules comprise or consist of, for instance, at least one flow reactor for heating, at least on flow reactor for cooling, at least one flow reactor for photochemical reactions, at least one flow reactor for microwave irradiation, at least one flow reactor for electrochemical reactions, at least one flow reactor that is a tube-in-tube reactor and at least one flow reactor that is a packed-bed reactor. Each continuous flow module further comprises at least one input and at least one output which are in fluid communication with the valve assembly system.

The reactor for heating consists according to the invention preferably of a PTFE tube reactor and of a heating system which may be an oven used in conventional gas chromatography systems and which allows temperatures between ambient temperature and 250° C. Alternatively, the reactor could be a stainless steel reactor for temperatures between ambient temperature and 350° C. All homogeneous reactions that require elevated temperatures can be carried out in a reactor for heating. The reactor for cooling preferably comprises a PTFE tube reactor, which is suspended in a cold batch controlled by an external chilling unit that can cool down to −40° C. Alternatively, the PTFE tube reactor is cooled by a dry ice heat exchanger down to −70° C. The reactor for cooling may further comprise an additional input with a precooling loop for mixing reagents directly in the flow reactor. All homogeneous reactions that need cooling can be conducted in a reactor for cooling. The reactor for photochemical reactions consists of a PTFE tube reactor or a FEP tube reactor coiled around either a medium pressure Hg lamp or a LED. The photochemical reactor can be either heated or cooled. All homogeneous photochemical reactions can be performed in a reactor for photochemical reactions. The flow reactor for microwave irradiation consists of a PTFE tube reactor and a microwave oven. All homogeneous reactions that require microwave irradiation can be carried out in a reactor for microwave irradiation. In a tube-in-tube reactor homogeneous gas/liquid reactions can be performed. The tube-in-tube reactor consists of a tube surrounding a gas permeable inner tube through which the reagents flow passes. By controlling the pressure of the gas, the solution can be saturated without the need for a gas/liquid separator following the reactor. The tube-in-tube reactor can be placed in a variable temperature bath. In a packed-bed reactor heterogeneous transformations where reagents are on solid support or insoluble catalysts can be run. The packed-bed reactor can also be used to leach reagents into solution. The packed-bed reactor consists of an array of columns that are connected to the flow of reagents through a switch valve. The columns can easily be replaced, when they are consumed. The columns can be further heated or irradiated by a photo lamp, when necessary. In a preferred embodiment according to the present invention the reactors can house up to 15 milliliters.

The following reactions can be carried out, preferably but not exclusively, by the continuous flow modules that may be comprised by the modular continuous flow device according to the present invention: oxidation, biphasic oxidation, epoxidation, olefination, aminolysis, hydrogenation, reduction, Michael addition, hydrolysis, introduction of protecting groups, cleavage of protecting groups, singlet oxygen reactions, etherification, click reactions, acid-mediated cleavage, esterification, saponification, photooxidation, nucleophilic substitution, radical substitution, activation of carboxylic acids, Knoevenagel, Horner-Wadsworth-Emmons and Wittig reaction.

The modular continuous flow device according to the invention comprises between 4-15 continuous flow modules, preferably 5-12 continuous flow modules and more preferably 6-10 continuous flow modules. Alternatively, the modular continuous flow device comprises at least 4, preferably at least 5, more preferably at least 6, even more preferably at least 7, even more preferably at least 8, even more preferably at least 9, and most preferably at least 10 continuous flow modules.

As explained above, all continuous flow modules are arranged in parallel and are connected through an inlet and through an outlet to the valve assembly. The modular continuous flow device may in addition contain further modules which do not necessarily have that parallel connection. Such modules are the final product collector which is for collecting and probably storing the final product, detector modules which can be positioned at any place within the modular continuous flow device or workup modules which are preferably positioned between the outlet of a continuous flow module and the valve assembly.

Flow Reactor for Intermediate Product Storage

In a preferred embodiment one continuous flow module of the modular continuous flow device is a reactor for intermediate product storage. This reactor allows that an intermediate product which is not subsequently reacted in the next step of the reaction sequence can be stored in that reactor for intermediate product storage preferably under continuous flow conditions until the intermediate product is used in the reaction sequence. This intermediate product is also called "sub route product" in order to distinguish this intermediate product which is an intermediate product which will be used in the synthetic main route and which is not a starting material and which has to be simultaneously synthesized while at the same time the main route intermediate product is synthesized which will be reacted with the sub route product in one step of the main reaction sequence.

Consequently the term "main route intermediate product" refers to the intermediate product of the synthetic main route which will be reacted with the sub route product.

The "synthetic main route" is the reaction sequence from the starting material to the final product.

The "synthetic sub route" refers to a reaction sequence by which a sub route product is synthesized and not the final product.

All other chemical compounds obtained during the reaction sequences are called "intermediate products" if they are not a sub route product and not a main route intermediate product and of course also not a final product.

This flow reactor for intermediate product storage provides the huge advantage that a sub route product can be prepared in advance by a synthetic sub route and can be stored in that flow reactor for intermediate product storage until the synthetic main route reached the step where the main route intermediate product has to be reacted with the sub route product. The synthesis of the sub route product will be carried out under continuous flow conditions. The storage of the sub route product in the flow reactor for intermediate product storage will preferably be under continuous flow conditions. The synthesis of the final product through the synthetic main route will also be performed under continuous flow conditions. Such a way to synthesize the final product allows that continuous flow modules can be used twice, in the synthesis of the sub route product and also in the synthesis of the final product.

The at least one flow reactor for intermediate product storage has a further huge advantage. Not only the sub route product but any intermediate product including the main route intermediate product could temporarily be stored in that flow reactor for intermediate product storage in case the flow rate should be increased or decreased during the next reaction step in the next continuous flow module. In case, the processed volume of the reaction solution should not be altered and the flow rate should be decreased, the part of the volume which cannot be processed can temporarily be stored in the flow reactor for intermediate product storage. On the other hand, if the processed volume shall remain the same and the flow rate shall be increased during the next step; more volume of the reaction solution will pass the next step than is delivered by the current step. In that case, the volume of the reaction solution of the current step will not directly be fed into the next continuous flow module. The obtained volume of the reaction solution will first be accumulated in the flow reactor for intermediate product storage until a sufficient volume of reaction solution is present in the flow reactor for intermediate product storage which can be processed with the higher flow rate through the next continuous flow module. None of the state of the art devices is able to provide such advantages.

The inventive device comprising a flow reactor for intermediate product storage is particularly useful for performing convergent chemical reaction sequences. FIG. 4 illustrates a convergent multistep synthesis that is divided into the synthetic main route (19) with the reaction steps 24a-24e and two synthetic sub routes 18a and 18b with reaction steps 24f-24h respectively 24i and 24j. The first two reaction steps of the synthetic main route 24a and 24b are carried out simultaneously with the synthetic sub route 18b or the synthetic sub route 18b is run first and the sub route product 23b is stored in the module for intermediate product storage. Subsequent reaction step 24c of the synthetic main route is carried out with the main route intermediate 22a and sub route product 23b provided from the module for intermediate product storage. At the same time the synthetic sub route 18a is carried out and sub route product 23a stored in the module for intermediate storage while the synthetic main route is further conducted to main route intermediate product 22b. In the last reaction step 24e the final product (25) is formed from the intermediate product 22b and sub route product 23a provided from the flow reactor for intermediate product storage. FIG. 4 illustrates a convergent multistep synthesis consisting of one synthetic main route and two synthetic sub routes. In general a convergent multistep synthesis can also contain only one synthetic sub route or even more than one or two synthetic sub routes.

For a convergent synthesis at least one main route intermediate product and at least one sub route product, each prepared by different synthetic routes, are required. However, when the reactions are run sequentially the sub route product must be stored until the main route intermediate product is synthesized. When sub route products are reactive substances, sensitive to air or moisture and thus not shelf-stable, it is necessary to run reactions parallel to keep storage times short. This means that a device according to this invention can perform convergent multistep synthesis by running single reaction steps parallel and by storing sub route products.

Thus the inventive modular continuous flow device comprising a flow reactor for intermediate product storage has the huge advantage over the state of the art devices that convergent chemical reaction sequences can be carried out which require the synthesis of at least one intermediate product by at least one reaction step, storing this intermediate product or synthesizing this intermediate product simultaneously with the synthetic main route and introducing this synthesized, that means pre-synthesized and stored or simultaneously synthesized, intermediate product into the reaction sequence whenever needed. Consequently the inventive modular continuous flow device allows, for instance, the three-step synthesis of a sub route product by a synthetic sub route and simultaneously or subsequently the four-step synthesis of a main intermediate product by a synthetic main route, reacting the synthesized main intermediate product with the stored or simultaneously synthesized sub route product to a further intermediate product which is in two further reaction steps converted to the final product and this complete reaction sequence, i.e. the synthetic main route and the synthetic sub route is performed in a continuous flow manner and is performed in a modular continuous flow device which could after synthesizing the desired amount of the final product without deconstruction or without rearrangement of the continuous flow modules be used for a different reaction sequence just by using the continuous flow modules in another order.

The flow reactor for intermediate product storage is preferably a PTFE tube reactor that can house at least 15 millilitres. The input and the output of the flow reactor for intermediate product storage are connected to the valve assembly over two different fluid connections. The flow reactor for intermediate product storage can be used for storing a sub route product (23) within a convergent multi-step synthesis. This sub route product is subjected later to the further transformation with the main route intermediate product (22) and optionally other reagents. While storing an intermediate product which is not a sub route product, time is given for adjusting reaction conditions of the continuous flow modules, especially when one continuous flow module is used consecutively under different conditions such as different flow rates or temperatures. Furthermore, time is given for running other reactions parallel and time is also given for maintaining the device by exchanging expired columns of a packed-bed reactor, if present or by replacing malfunctioning continuous flow modules without stopping the reagent flow. In addition, the flow reactor for intermediate product storage (5) may also be used for performing reactions at ambient temperature, when it is a PTFE tube reactor. The modular continuous flow device is run under continuous flow conditions and due to the finite length of the continuous flow module the storage time may be limited.

However, this can be circumvented when an infinite loop is installed. An infinite loop can be realized for instance when two PTFE tube reactors are connected linearly to each other through a multiport switch valve. The switch valve switches continuously in defined intervals between two positions so that the flow of reagents is passed between the two PTFE tube reactors without changing the flow direction and solvent enters and leaves the infinite loop continuously. When the continuous switching stops, the flow of reagents exits the infinite loop.

Thus, in one embodiment of the present invention the modular continuous flow device comprises:
a) a plurality of continuous flow modules and at least one flow reactor for intermediate product storage;
b) a reagent supply system;
c) a valve assembly;
d) means for controlling flow rates and/or pressure;
wherein each continuous flow module is connected to the valve assembly by at least one inlet and by at least one outlet and the reagent supply system is connected to the valve assembly and wherein the continuous flow modules are in a parallel arrangement.

In an alternative embodiment of the present invention the modular continuous flow device is a device for convergent synthesis comprising:
a) a plurality of continuous flow modules for performing chemical reactions and at least one flow reactor for intermediate product storage;
b) a reagent supply system for supplying the reagents;
c) a valve assembly for connecting the continuous flow modules to each other;
d) means for controlling flow rates and/or pressure;
wherein each continuous flow module is connected to the valve assembly by at least one inlet and by at least one outlet and the reagent supply system is connected to the valve assembly and wherein the continuous flow modules are in a parallel arrangement.

Workup Module

In another embodiment according to the present invention the modular continuous flow device for convergent synthesis further comprises at least one workup module (7). The workup module preferably consists of at least one liquid-liquid-extraction device. The workup module input and workup module output are preferably connected to the valve assembly over two different fluid connections. The liquid-liquid-extraction device comprises an additional input for an aqueous phase that is mixed with the flow of reagents prior separating both phases and a separator chip. The separator chip consists of one input and two outputs. Within the separator chip the two phases cross a hydrophobic PTFE membrane. The organic phase passes the membrane and is directed to the output of the workup module. The aqueous phase does not pass through the membrane and may be collected in an additional container or discarded to waste. According to the invention, the flow of reagents may pass the workup module after each reaction step or at the end of a reaction sequence. The workup module may also be passed by the flow of reagents consecutively multiple times in order to increase the purification. Of course, only one flow of reagents can pass the workup module at a given time.

The modular continuous flow device according to the invention comprises preferably two flow reactors for heating, further two continuous flow modules and a workup module and a detector module. More preferred are modular continuous flow devices that comprise one flow reactor for heating and one flow reactor for cooling, further two continuous flow modules and a workup module and a detector. Even more preferred are modular continuous flow devices that comprise one flow reactor for heating, one flow reactor for photoreactions, one further continuous flow module, and a flow reactor for intermediate product storage and workup module and a detector module. Especially preferred are modular continuous flow devices that comprise one flow reactor for heating and one flow reactor for cooling and one flow reactor for photoreactions and one flow reactor for intermediate product storage and one flow reactor which is a tube-in-tube reactor and one flow reactor which is a packed-bed reactor and one flow reactor for microwave irradiation and a workup module and a detector module and a flow reactor for purification.

The flow reactor for purification preferably but not exclusively comprises a Simulated-Moving-Bed-chromatography (SMB) unit which consists of several reversed-phase (RP-18) chromatography columns, a multiport valve switch, several preparative pumps and a UV-detector. The SMB-chromatography unit enables continuous purification of the crude reaction products due to the linear arrangement of the columns and the continuous switching of the columns opposite to the flow direction of the eluent. Thus purification of the crude reaction products and regeneration of the used columns is achieved simultaneously.

The flow reactor for purification is a continuous flow module and the flow reactor for intermediate product storage is also a continuous flow module and thus both have the inventive parallel connections to the other continuous flow modules through the valve assembly and are also arranged in parallel to all other continuous flow modules.

Thus, in an embodiment of the present invention the modular continuous flow device for multistep synthesis comprises:
a) a plurality of continuous flow modules,
b) a reagent supply system;
c) a valve assembly;
d) means for controlling flow rates and/or pressure; and
e) a workup module;
wherein each continuous flow module and the workup module are connected to the valve assembly by at least one inlet and by at least one outlet and the reagent supply system is connected to the valve assembly.

Parallel Arrangement

In addition to the connection between the reagent supply system and the valve assembly, there are according to the present invention at least two separate fluid connections between each continuous flow module and the valve assembly. Thus, the continuous flow modules are in a parallel arrangement.

Preferably each continuous flow module of the plurality of continuous flow modules is connected to the valve assembly. More preferably each continuous flow module of the plurality of continuous flow modules is connected to the valve assembly by one inlet and one outlet.

Each continuous flow module is separately connected to the valve assembly so that a flow of reagents is directed from one output port for each continuous flow module of the valve assembly to the input port of each continuous flow module and so that a flow of reagents is directed from the output port of each continuous flow module to an input port for each continuous flow module of the valve assembly. Therefore the continuous flow modules are indirectly connected to each other via the valve assembly. This enables in detail (a) directing a flow of reagents from the reagent supply system via the valve assembly to one continuous flow module, (b) directing a flow of reagents from one continuous flow module via the valve assembly to another continuous flow module, (c) directing a flow of reagents from a continuous flow module via the valve assembly to the same continuous flow module, (d) directing a flow of reagents from one continuous flow module via the valve assembly to the flow reactor for intermediate product storage, (e) directing a flow of reagents from the flow reactor for intermediate product storage via the valve assembly to another continuous flow module and (f) directing a flow of reagents from one continuous flow module via the valve assembly to the final product collector (31). Hence, a multistep synthesis is carried out by directing one flow of reagents consecutively to the different continuous flow modules or to the same continuous flow module repeatedly or by directing two or more flow of reagents to two or more different continuous flow modules in that way, that no more than one flow of reagents is directed at a given time to a specific continuous flow module. In other words the valve assembly can be positioned so that it directs a flow coming from any input port to any output port. However, only one flow can be directed to a specific output port at a given time.

The valve assembly in combination with the parallel arranged continuous flow modules provides a highly flexible setup for conducting any multistep synthesis. Due to the variety of different continuous flow modules, virtually any condition can be applied to a reaction under continuous flow conditions. The repeated use of any continuous flow module enables running even longer synthesis without increasing the number of continuous flow modules. However, this can also be achieved by controlling the flow rate of the solvent. Unlike the state of the art, the modular continuous flow device has the ability to modulate the flow rate, and thus the residence time, for later steps of a multistep sequence.

In contrast to the state of the art, it is possible to carry out several multistep syntheses with one fixed setup. No reassembling of the device and no extension or removal of continuous flow modules is necessary. While this is a benefit for multistep syntheses consisting of 4 or more reaction steps, shorter reaction sequences may be carried out efficiently with other systems.

Valve Assembly

The valve assembly which is comprised by the modular continuous flow device according to the invention preferably consists of multiple input ports, multiple output ports, multiple port switch valves connecting the input ports with the output ports and a junction. Preferably the valve assembly consists of at least one multiport switch valves equipped with a mixer and/or equipped with a splitter. Any input port can be connected to any output port by positioning the switch valves. A connection between two different input ports is not possible and a connection between two different output ports is also not possible. An input port is a port at which a fluid enters the valve assembly and an output port is a port at which a fluid leaves the valve assembly. Only one connection can be established from one input port to one output port at the same time. More than one connection between different input ports and different output ports can be established simultaneously. Preferably a connection between two or more different input ports and one output port is not possible. Also preferably a connection between one input port and two or more output ports is not possible. The valve assembly is in fluid communication with the reagent supply system and the continuous flow modules. As the movement of the flow of reagents has a direction, this specific direction should not be reversed. Thus, the flow of reagents from the reagent supply system is always directed towards the valve assembly and therefore the reagent supply system is connected to the valve assembly through an input port. Each continuous flow module is connected to the valve assembly through an output port at which the flow leaves the valve assembly and enters the continuous flow module and each continuous flow module is connected to the valve assembly through an output port at which the flow coming from the continuous flow module enters the valve assembly. With this, the continuous flow modules are connected to each other indirectly through the valve assembly. Also each continuous flow module is connected to itself via the valve assembly so that a flow can pass a single continuous flow module repeated times. As pointed out above only one flow of reagents can pass a continuous flow module at a given time due to the parallel arrangement of the continuous flow modules. However, multiple flows of reagents may pass multiple continuous flow modules simultaneously which enables running reactions simultaneously.

The valve assembly according to the invention preferably further comprises a junction for joining and mixing different flows. The junction is preferably a three-way junction which is connected to two output ports and one input port of the valve assembly. Between the three-way junction and the input port of the valve assembly may be a static inline mixer installed for ensuring homogeneity of the combined flow. The three-way junction allows for joining together two flows coming from different continuous flow modules and allows for joining together one flow coming from a continuous flow module and a flow coming from the reagent supply system and allows for joining together two flows coming from the reagent supply system. By directing the combined flow back to the junction, more flows may be joined together sequentially.

The valve assembly according to the invention preferably further comprises a flow splitter for splitting one flow into two flows. The flow splitter may be fixed to a specific flow ratio or adjustable within a specific range of flow ratios. The flow splitter has one inlet port that is connected to an output port of the valve assembly and the flow splitter has two outlet ports which are connected to two different input ports of the valve assembly. The flow splitter allows for dividing a flow of reagents coming from a continuous flow module or coming from the reagent supply system into two flows of reagents of the same composition. The divided flows of same composition can then be directed to two different continuous flow modules, i.e. two reactors, one reactor and one detector module.

In one embodiment of the present invention wherein one continuous flow module is a reactor for intermediate product storage, the valve assembly is adapted to allow the simultaneous use of two or more continuous flow modules so that in one or in one part of the continuous flow modules intermediate products of a synthetic main route and in another or in another part of the continuous flow modules intermediate products of a synthetic sub route can be synthesized.

Reagent Supply System

The reagent supply system of the modular continuous flow device may consist of one or more reagent supply sub-systems. Each reagent supply system or reagent supply sub-system may consist of several reagent containers for storing each reagent and/or solvent, a reagent selector (9) which is a multiport switch valve for accessing the reagent containers and means for withdrawal (11) of the reagents or solvents. A mean for withdrawal (11) is preferably a syringe or a syringe pump. The reagent containers (17) are pressurized and may be cooled, if necessary.

The system is not limited to liquid reagents. Solid or gaseous neat reagents can be used as solutions when they are dissolved first. Each reagent container is in a separate fluid connection to the reagent selector (9) and the reagent selector is in fluid connection to one or more means for withdrawal, so that the reagent selector can direct every reagent to one or more means for withdrawal. Further a container (10) containing a wash solution is also in fluid connection to the reagent selector. A reagent or solvent is transferred from the reagent container through the positioned reagent selector to a mean for withdrawal. The lines are then flushed with a wash solution from the container that contains the wash solution to avoid contamination prior to withdrawal of the next reagent or solvent. Contaminated solvent and used wash solution is collected in the waste container (16). In a preferred embodiment the reagent is then transferred to the valve assembly via an injection loop (13). FIG. 3a illustrates this connection. The reagents are pumped by a solvent from a container containing the solvent (12) through the device. Several injection loops may be in operation, allowing for multiple reagents or solvents to be fed into the device valve assembly simultaneously. This also allows for control of the reagent concentration. Reagents may be stored as concentrated solutions in their respective reagent containers. A volume of concentrated solution can then be transferred to the injection loop, while a separate injection loop contains the diluting solvent. As such, when the two are mixed prior to entering the valve assembly, a solution of desired reagent concentration, different from the concentration of the stored concentrated solution of the reagent, is delivered to the valve assembly. Preferably the reagent supply system is connected to the valve assembly by one or more inlets and can be connected to at least one continuous flow module by one or more inlets. It is obvious that such continuous flow modules which require specific reagents to convert the starting material, an intermediate product, the main route intermediate product with the sub route product should have a direct connection to the reagent supply system or a connection not involving the valve assembly.

The modular continuous flow device may also comprise a charging station (FIG. 3b). The charging station is in fluid connection to multiple sample loops (14). Reagents are loaded from the reagent supply system (2) into these sample loops prior transferring them to the valve assembly. Different reagents are stored in different sample loops. A solvent container (12) is connected to the charging station (15) providing solvent for the continuous flow.

Thus, preferably the reagent supply system is connected to an input port of the valve assembly through an injection loop or through a charging station.

Continuous and Convergent

The modular continuous flow device according to the present invention is a device that can perform multistep syntheses under continuous flow conditions. The inventive modular continuous flow device comprising a flow reactor for intermediate product storage is a device suitable for performing convergent syntheses under continuous flow conditions. Thus, preferably the modular continuous flow device provides the opportunity for performing convergent multistep syntheses under continuous flow conditions. Therefore, in a preferred embodiment of the present invention the modular continuous flow device comprises one, two or more flow reactor(s) for intermediate product storage.

Normally a predetermined amount of a final product shall be prepared. This requires starting with a certain volume of a solution of the starting material. This volume of the starting material is then processed through the modular continuous flow device in a continuous manner. In advance it might be required to synthesize one or more sub route product(s) which is/are stored in one or more flow reactor(s) for intermediate product storage.

Thus, the term "continuous" refer to the synthesis of a predetermined amount of a final product starting with a volume of a solution of a starting material required to obtain the predetermined amount of the final product by processing this volume through the modular continuous flow device in a continuous manner.

The term "continuous flow conditions" as used herein means a stream or flow, the so-called "flow of reagents" or "reagent flow", is passing through the modular continuous flow device constantly and the desired final product is obtained at the outlet of the modular continuous flow device in the final product collector. The flow of reagents may contain starting material, intermediate product(s), main route intermediate product(s), sub route product(s), final product, reagent(s) or solvent(s). The term "continuous flow conditions" means also that a reaction or reaction sequence is not performed batch-wise. While the flow passes the modular continuous flow device other flows containing reactants, reagents or solvents may join the first flow. Also one flow may be split into two flows in the modular continuous flow device. The term "continuous" as used herein defines that the flow is always moving. The flow rate may be constant over the reaction time, may vary, may be increased and decreased continuously or may stop for a short period of time. The movement of the flow has a direction which should not be changed, namely from the starting material to the final product. Syntheses can be performed under continuous flow conditions in basically two different ways: On the one hand, starting material enters the device steadily and the final product is collected at the outlet of the device permanently without dividing the reaction mixture into parts. On the other hand, the reactants are in defined segments of the flow. The segments have a finite volume and are surrounded by a solvent. The segments are pushed by the solvent through the modular continuous flow device. In order to minimize dilution of the segments, the solvent should be immiscible or an additional immiscible solvent like a perfluorinated hydrocarbon is added to the borders of each segment. The use of immiscible solvents also reduces dispersion effects, which arise especially in multistep syntheses. Another possibility to minimize dispersion as well as dilution is the use of a solvent as carrier fluid with which the reactants are soluble, and dispersion as well as dilution can be minimized through the use of inline mixers placed before and/or after each continuous flow module. In addition the segmentation of the continuous flow enables the use of harsh reagents such as hydrogen chloride and sulfuric acid, because the system components are not exposed to these reagents permanently. The throughput of the latter approach is higher due to the segmentation that enables mixing multiple segments and injecting them in a serial or parallel fashion.

Continuous flow chemistry in general enables the use of extreme reaction conditions, like high temperatures, pressures and microwave irradiation without serious safety concerns. Reaction parameters like temperature can be efficiently controlled and adjusted precisely over the reaction time and therefore higher yields and selectivities are achieved. Automation of continuous flow reactions is far simpler and it allows for unattended operation and experimental planning. Multi-step reactions can be conducted continuously, which is advantageous for unstable, air-sensitive or toxic intermediates. In addition important purification techniques like chromatography, crystallization, or liquid-liquid extraction can be coupled with processes under continuous flow conditions.

As used herein the term "divergent syntheses" or "diversity oriented synthesis" refers to multistep syntheses of at least two different final products synthesized from one common main route intermediate product. Typically the final products have the same or a similar core structure or skeleton that is already part of the common main route intermediate product. The common main route intermediate product is formed typically at a late stage of the multistep synthesis and diversification is achieved by reacting the common main route intermediate product with different reagents and/or different reaction conditions.

Fluid Connection

The present invention relates also to a modular continuous flow device for multistep synthesis comprising or consisting of:
a) a plurality of continuous flow modules;
b) a reagent supply system;
c) a valve assembly;
d) means for controlling flow rates and/or pressure;
e) means for fluid connection of the reagent supply system and the plurality of continuous flow modules to the valve assembly;

wherein each continuous flow module of the plurality of continuous flow modules is connected to the valve assembly by at least one inlet and by at least one outlet and the reagent supply system is connected to the valve assembly. The fluid connections between the individual components of the modular continuous flow device are established preferably by flexible PTFE tubes. The tubes are connected to the valves, to the input and output of each continuous flow module by suitable fittings in such a way that the fluid connections are tight and high pressures can be applied. The fittings are made of non-corroding material. Alternatively, stainless steel capillaries may be used for establishing fluid connections and as reactor coils, allowing for better heat exchange and higher temperatures/pressures to be reached.

Means for Controlling Flow Rates and/or Pressure

The modular continuous flow device according to present invention further comprises means for controlling flow rates and/or pressure. Means for controlling flow rates and/or pressure are preferably pressure regulators or back pressure regulators. By regulating the pressure and/or the back pressure the flow rate can be adjusted. Pressure regulators are preferably installed before the valve assembly or at the output of each continuous flow module. The flow rate is controlled by regulating or reducing undesirably high pressure which is achieved by adjusting a valve. A back pressure regulator is preferably installed at the outflow the device providing an obstacle to the flow and thus regulating the (back) pressure.

The means for controlling flow rates and/or pressure can be one mean which does both or can be a mean for controlling the flow rate or can be a mean for controlling pressure. However an increased flow rate will normally result in an increased pressure and increased pressure will result in an increased flow rate.

Means for controlling flow rates and/or pressure are preferably the pump driving the solvent, and thus the flow of reagents, through the modular continuous flow device, as the flow of reagents is divided into isolated segments and solvent in between. By manipulating the rate of the pump, the residence time of the flow of reagents within the modular continuous flow device is thus controlled. As such, for example if the desired flow rate for the second (or any later-stage) transformation is slower than the flow rate in the previous step, the flow rate of the solvent (driven by the pump) can be decreased.

In an embodiment of the present invention wherein one continuous flow module is a reactor for intermediate product storage, the opposite is also possible. If a large discrepancy between flow rates of consecutive steps is required, the flow of reagents can pass through the flow reactor for intermediate product storage, allowing for the entire reagent flow to exit the previous flow reactor at the same flow rate. The flow rate can then be adjusted, increased or decreased, to the stream in the flow reactor for intermediate product storage, and once at the correct flow rate it can enter the next continuous flow module. The flow rate can also be dropped significantly to allow for time to change conditions in a station or to replace a packed bed reactor. This ability to slow (or speed up) flow rates in late-stage transformations in multistep sequences is unique as compared to the state of the art.

The means for controlling flow rates and/or pressure are preferably adapted to use a different flow rate and/or a different pressure in each continuous flow module.

Detector

The modular continuous flow device may further comprise at least one detector (6) for monitoring the reaction progress. The detector is preferably a FTIR-spectrometer or an UV-spectrometer, suitable for continuous analyzing the flow of reagents. The detector has one input and one output which are connected to the valve assembly over two different fluid connections. However, only one flow of reagents can pass the detector at a given time. By measuring IR or UV absorption, the detector enables monitoring of the reaction progress after each reaction step and at the end of a reaction sequence and further enables optimization of individual reaction steps.

System Controller

The modular continuous flow device may further comprise at least one system controller (8) for controlling and monitoring the chemical synthesis. The system controller preferably comprises communication buses to all components of the device, namely all multiport switch valves, the valve assembly, the pump system, the means for withdrawal, the means for controlling the flow rate, each continuous flow module, the reactor for intermediate product storage, the workup module and the detector. Further the system controller is connected to a computer and may be controlled by a computer program. Every component of the device is controlled by the system controller. Reactions may be run in an automated fashion by the computer program. Reactions may be optimized by the computer program in conjunction with the detector.

Mixer

The modular continuous flow device may further comprise a plurality of mixers. Mixers enable reduction of dispersion of the flow of reagents which is necessary especially in multistep syntheses. The mixers employed according to the present invention are preferably but not exclusively static inline mixers and they consist of PTFE, glass, stainless steel or PVC. Homogeneity of the flow of reagents is ensured by alternating movement of the flow of reagents through the static mixers. The static mixers do not consist of moving parts and is therefore nearly maintenance free. The mixers may be installed as a part of a fluid connection at the output of each continuous flow module and if necessary may also be a part of a continuous flow module. In addition mixers may be placed between the reagent supply system and the valve assembly in order to mix reagents prior passing them to the continuous flow modules.

Thus, the modular continuous flow device preferably further comprises mixers preferably installed at the output of each continuous flow module for reducing dispersion effects.

The modular continuous flow device according to the present invention is a device that can perform multistep syntheses that consist of at least 4 reaction steps, preferably at least 5 reaction steps, more preferably at least 6 reaction steps, even more preferably at least 7 reaction steps and most preferably at least 8 reaction steps. The maximum number of reaction steps in a multistep synthesis is not limited by the device.

One important aspect of the modular continuous flow device according to the present invention is the simultaneous performance of reaction steps in different continuous flow modules. Although in a continuous flow module several reactions can be carried out sequentially, only one reaction can be carried out at a given time. Therefore, for simultaneous synthesis different continuous flow modules are required. The different continuous flow modules may be of different type or of the same type (for instance two reactors for heating, where one is set to 40° C. and the other to 80° C.). For instance a three-step convergent synthesis that necessarily consists of a two-step main route and a single-step sub route is conducted so that the first two reaction steps are run simultaneously in different continuous flow modules (e.g. a photo reactor and a heating reactor) followed by the third reaction step. The continuous flow modules I, II and III for the respective reactions (24*a-c*) are set to provide the required reaction conditions (e.g. heating, irradiation or cooling). The starting material for the main route (20*a*) is delivered from the reagent supply system to the valve assembly either directly or via a sample loop of the charging station. Additional reagents are added to the starting material and mixed in the valve assembly. The valve assembly is set to load the reaction mixture to the continuous flow module I. At the same time, starting material for the sub route (20*b*) and reagents are provided from the reagent supply system in the same way and loaded into the valve assembly. The valve assembly is now set to direct the sub route reaction mixture containing starting material (20*b*) to the continuous flow module II without interrupting the flow passing the continuous flow module I. At this particular moment both reaction steps (24*a*) and (24*b*) are carried out in different continuous flow modules, namely I and II. When both reaction mixtures containing sub product and main route intermediate enter the valve assembly again, they are joined together with reagents delivered from the reagent supply system for the third reaction step (24c) in the valve assembly. The reaction mixture is then loaded from the valve assembly to the continuous flow module III, where the third reaction step to the final product proceeds. The crude final product (25) enters again the valve assembly from where it can be submitted to further modules for workup, purification or to a detector for analytics or to the outlet of the device.

Another important aspect of the inventive modular continuous flow device comprising a flow reactor for intermediate product storage is the ability to store sub route products during a convergent multistep synthesis. A convergent multistep synthesis where each reaction step is conducted sequentially and not simultaneously and where each synthetic sub route is conducted prior to the synthetic main route requires storing the sub route product and combining it with the main route intermediate product for convergent synthesis. For instance, a convergent three-step synthesis is performed sequentially so that at first the sub route product is formed and stored and then main route intermediate product is formed and combined with stored sub route product and brought to reaction to the final product. In detail, starting material (20b) and reagents for the synthetic sub route (18) are delivered from the reagent supply system either directly or via a sample loop of the charging station to the valve assembly. The continuous flow modules I, II and III are set to provide the required reaction conditions for reactions (24a-c). If two reactions are carried out in the same continuous flow module sequentially, the reaction conditions for the second step are set after the first reaction is completed. The valve assembly is positioned so that the reaction mixture for the first reaction is loaded to the continuous flow module I. When the reaction is completed the sub route product (23) is directed back to the valve assembly and the valve assembly submits the sub route product to the continuous flow module for intermediate storage where it resides until the main route intermediate product (22) is formed. Therefore, starting material (20a) and reagents for the first reaction step (24a) of the main route are delivered from the reagent supply system in the same way, combined and mixed in the valve assembly. The valve assembly directs the reaction mixture to the continuous flow module II and the main route intermediate product (22) is formed. The main route intermediate product and the stored sub route product are submitted back to the valve assembly where both compounds are joined together with the reagents for the third reaction step (24c) and loaded to the third continuous flow module III. After the reaction is completed, the crude final product (25) enters again the valve assembly from where it can be submitted to further modules for workup, purification or to a detector for analytics or to the outlet of the device.

In a preferred embodiment of the inventive modular continuous flow device comprising a flow reactor for intermediate product storage, the device is applied in the convergent synthesis of the artemisinin derivate (30) under continuous flow conditions. The details are given in Example 4 and the synthesis is shown in FIG. 8. In this particular embodiment, the modular continuous flow device comprises a continuous flow module for photo reaction, a continuous flow module with a tube-in-tube reactor, a continuous flow module with a packed-bed reactor, a continuous flow module for intermediate product storage, a workup module, a detector module and a back pressure regulator. The synthesis consists of 4 reaction steps wherein the synthetic main route starting from dihydroartemisinic acid is three steps long and proceeds over artemisinin to the reduced dihydroartemisinin. The dihydroartemisinin is a main route intermediate product that is subsequently brought to reaction with the sub route product of the esterification of phenylpropionic acid with N-hydroxysuccinimide. Although the artemisinin synthesis includes 3 reaction steps, i.e. photooxidation with singlet oxygen, the acid-mediated cleavage and the oxidation with triplet oxygen, they are referred as a single step. The reagent supply system is provided with the required starting material and reagents for all reaction steps:

Exemplary Application of the Inventive Modular Continuous Flow Device to the Convergent Multistep Synthesis of an Artemisinin Derivate A solution of dihydroartemisinic acid, TFA and the photosensitizer dicyanoanthracene for the artemisinin formation as well as solutions of phenylpropionic acid, EDC and N-hydroxysuccinimide for the sub route product. Starting with the synthetic main route, the dihydroartemisinic acid mixture is delivered from the reagent supply system to the valve assembly. The valve assembly is set to direct the reaction mixture to the continuous flow module with a tube-in-tube reactor, which is saturated with oxygen. The dihydroartemisinic acid solution is saturated with oxygen and then passed via the valve assembly to the continuous flow module for photoreactions. The reactor for photoreactions is cooled before the oxygen saturated dihydroartemisinic acid solution is submitted and irradiated. Afterwards the reaction mixture is directed via the valve assembly to the module for intermediate product storage where it resides at room temperature and where the acid-mediated cleavage as well as the second oxidation takes place. After completion of the reaction, the crude artemisinin solution is directed back to valve assembly and submitted again through the continuous flow module with the tube-in-tube reactor which degasses the solution for removing excess oxygen. Back at the valve assembly, the artemisinin solution is combined with ethanol provided from the reagent supply system and is then directed to the continuous flow module with a packed-bed reactor for reduction of artemisinin to dihydroartemisinin. Simultaneously, the starting material and reagents for the synthetic sub route, i.e. phenylpropionic acid, EDC and NHS, are delivered from the reagent supply system to the valve assembly. After mixing the reagents, the valve assembly is set to pass the reaction mixture to the continuous flow module for intermediate product storage where it resides at room temperature until the reaction is complete and until the main route intermediate product dihydroartemisinin is prepared. When the formation of dihydroartemisinin is finished, the crude dihydroartemisinin solution is passed via the valve assembly to the workup module where it is washed. The washed dihydroartemisinin solution and the stored sub route product are directed back to valve assembly and are joined together with an amine base provided from the reagent supply system.

This reaction mixture containing the main route intermediate product and the sub route product is then passed through the continuous flow module for intermediate product storage where it resides at room temperature until the reaction to the final product is completed. The crude artemisinin derivative solution is at last directed via the valve assembly to the workup module where it is washed again. The artemisinin derivative is collected at the outlet of the device.

DESCRIPTION OF THE FIGURES

FIG. 3 shows two embodiments for loading reagents and/or solvents from the reagent supply system (2) to the valve assembly (3). In FIG. 3a the reagent supply system is connected via an injection loop (13) to the valve assembly. Ports for solvents from a solvent container (12) and waste to a waste container (16) ensure flushing the lines after each reagent injection in order to avoid contamination. FIG. 3b illustrates a setup where two reagent supplies are connected to the valve assembly over a charging station (15). The charging station is equipped with two sample loops (14) which can be loaded from either the same reagent supply system or from different reagent supply systems. The reagents may be stored in the sample prior submitting them to the valve assembly (3). Additional ports for solvent container(s) (12) and waste container(s) (16) ensure cleaning of the lines and the charging station after each reagent loading in order to avoid contamination.

The legend of FIG. 5 reads as follows:

|  |  |
| --- | --- |
| - - - - | communication bus |
| —— | fluid connection |
| ⋈ | two way non-return valve |
| ⌷ | reagent/solvent container |
| ⌷ | thermostat |

Figure 6:
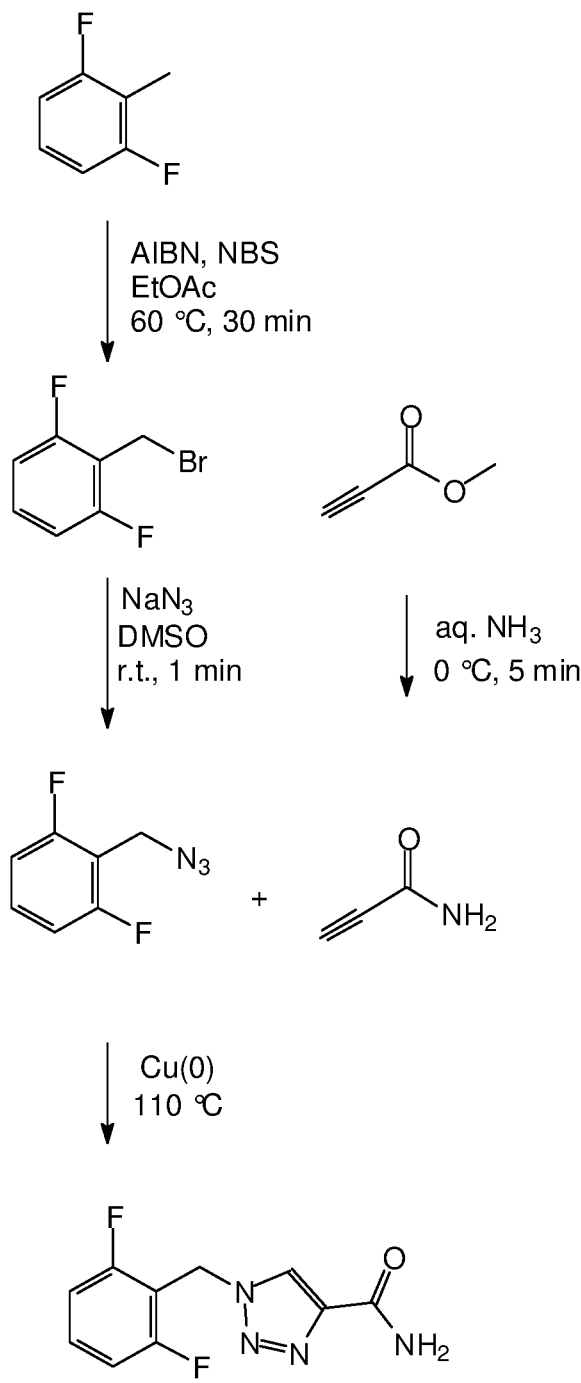

FIG. 6 shows the convergent multistep synthesis of rufenamide (28) starting from 2,6-difluorotoluene and methyl propiolate in 4 steps under continuous flow conditions.

Figure 7:
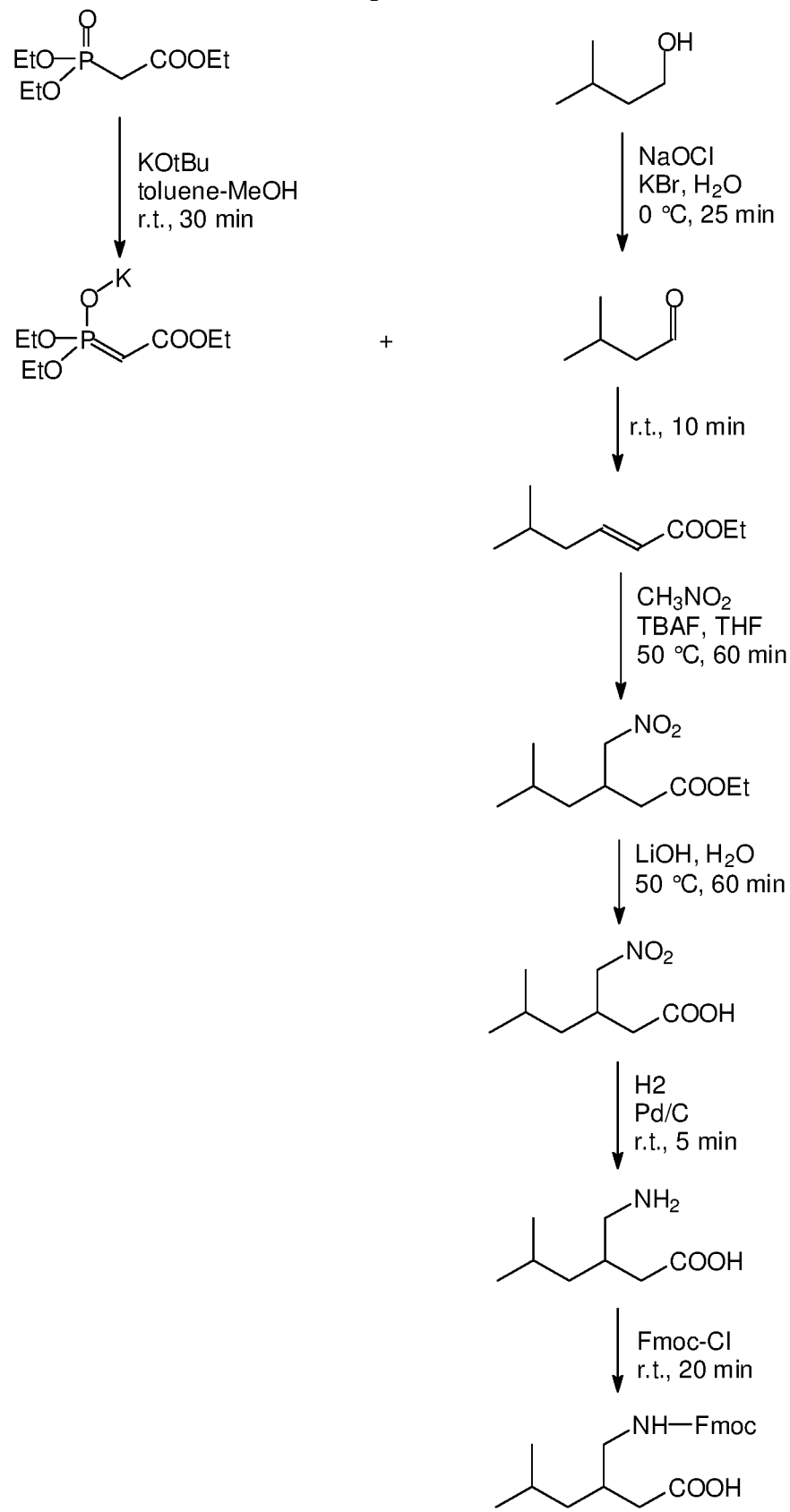

FIG. 7 shows the convergent multistep synthesis of N-Fmoc-protected pregabalin (29) from triethyl phosphonoacetate and isopentanol in 7 steps under continuous flow conditions.

Figure 8:
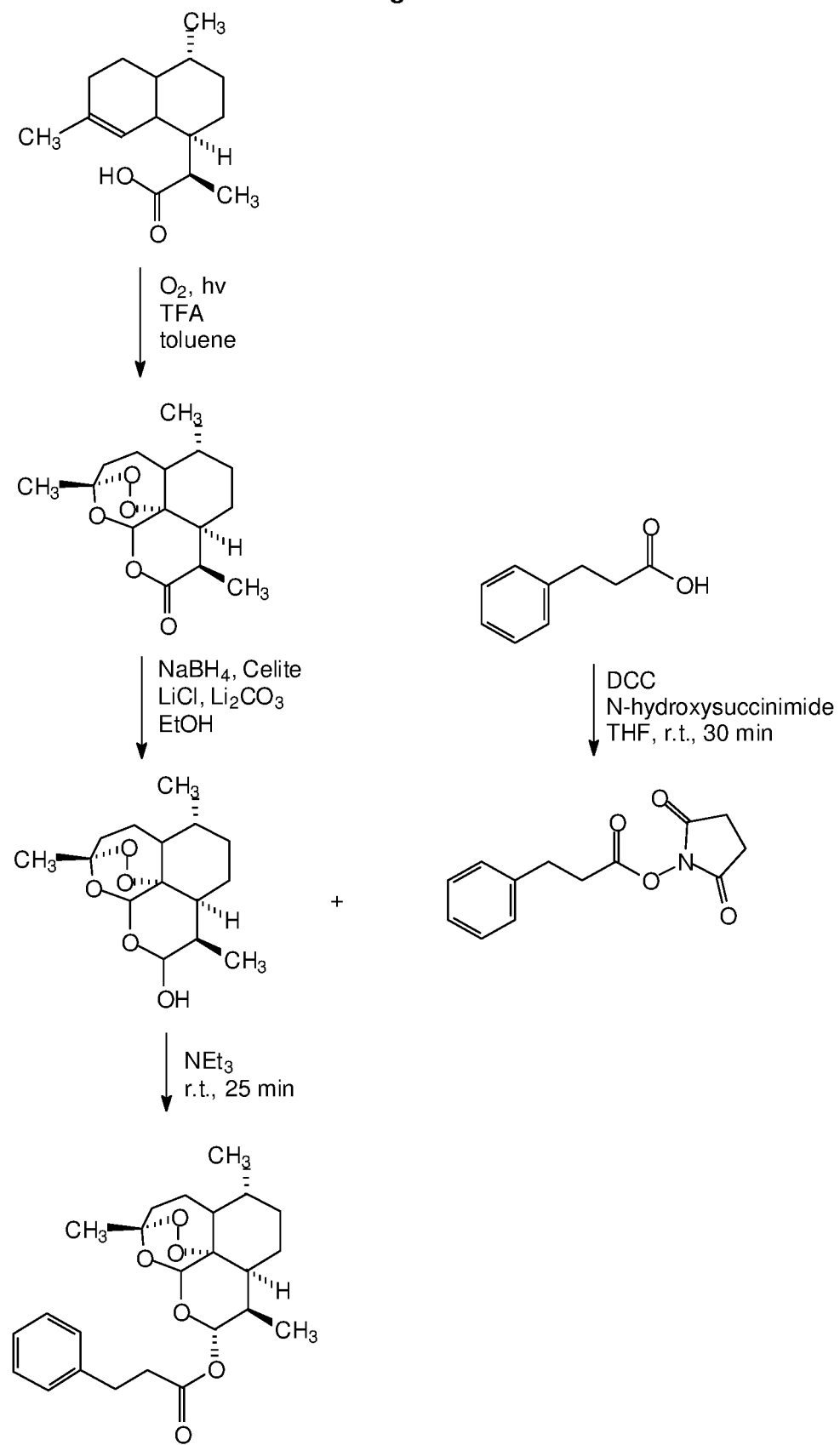

FIG. 8 shows the convergent synthesis of an artemisinin derivative (30) starting from dihydroartemisinic acid and phenylpropionic acid in 4 steps.

LIST OF REFERENCE SIGNS 1 continuous flow modules
2 reagent supply system
3 valve assembly
4 means for controlling flow rates and/or pressure
5 flow reactor for intermediate product storage
6 detector module
7 workup module
8 system controller
9 reagent selector
10 wash solution container
11 means for withdrawal
12 solvent container
13 injection loop
14 sample loop
15 charging station
16 waste container
17 reagent container
18 synthetic sub route
19 synthetic main route
20 starting material
21 intermediate product
22 main route intermediate product
23 sub route product
24 reaction step
25 final product
26 computer
27 pump
28 rufenamide
29 N-Fmoc-protected pregabalin
30 artemisinin derivative
31 final product collector

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

Example 1: Representative Modular Continuous Flow Device Setup for Automated Convergent Multistep Synthesis (FIG. 5)

Figure 1:
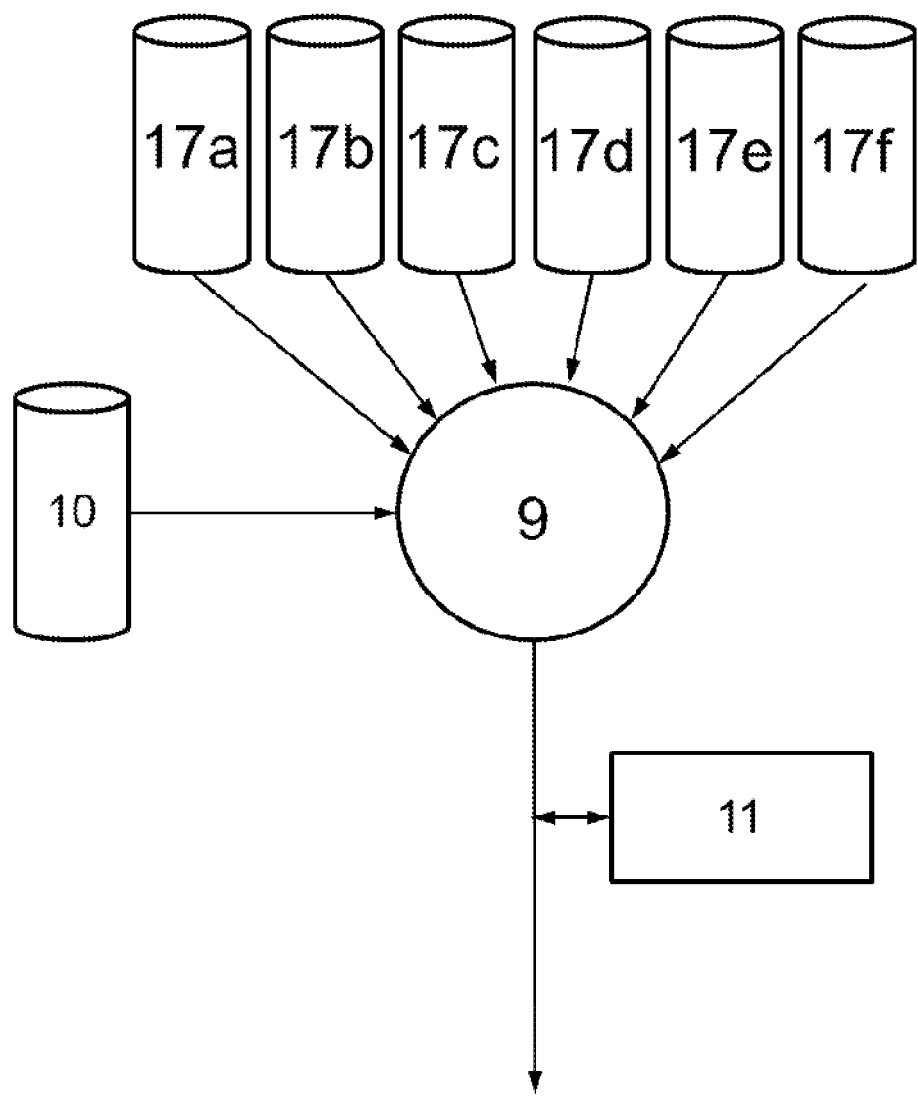
FIG. 1 shows a schematic drawing of a reagent supply system (2) of the state of the art that comprises several reagent containers (8), a reagent selector (9), wash solution container (10), means for withdrawal (11) and an outlet.
Figure 2:
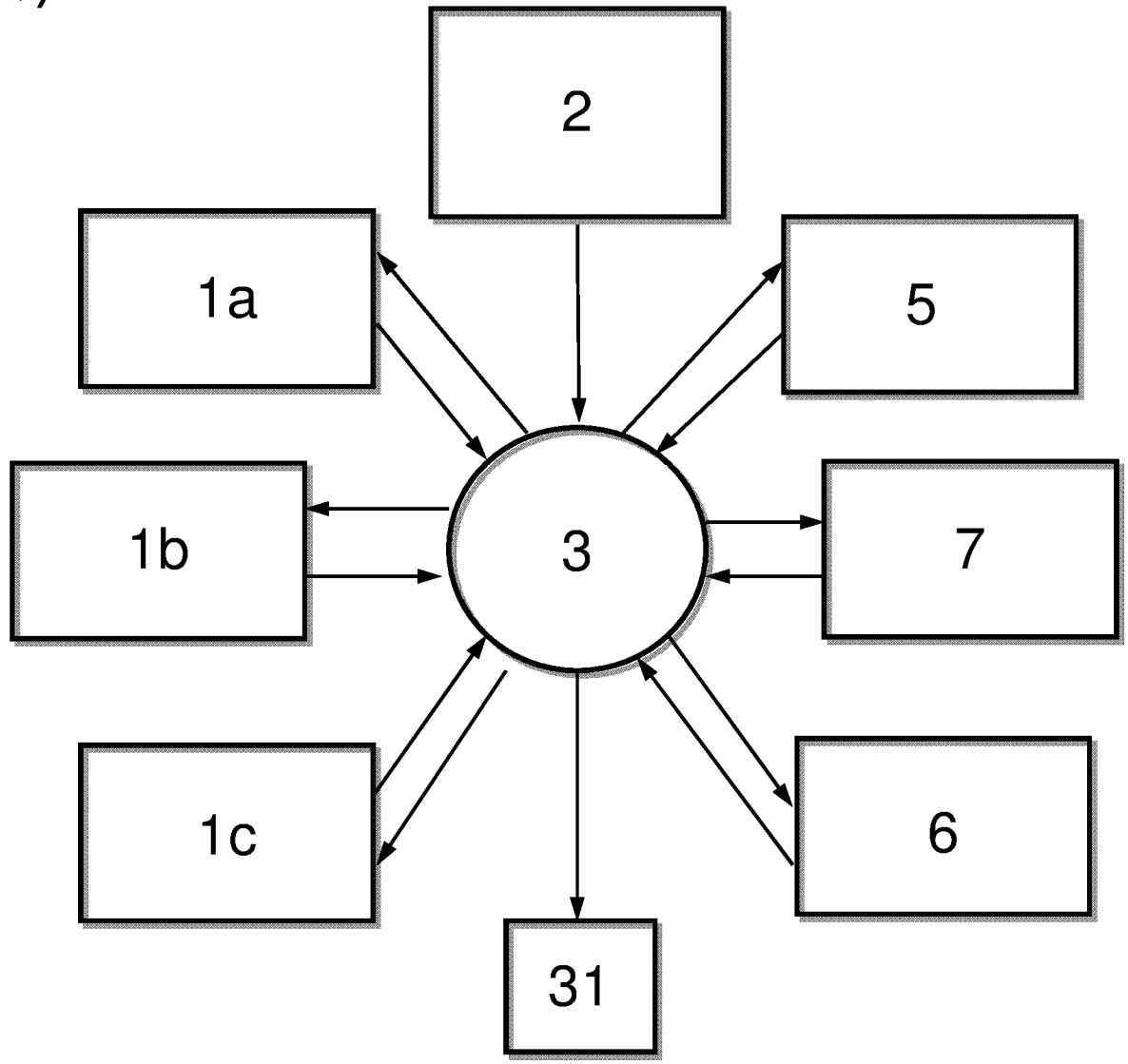
FIG. 2 a) shows a schematic drawing of an embodiment of the modular continuous flow device comprising three continuous flow modules (1), a reagent supply system (2), a valve assembly (3), a final product collector (31), a continuous flow module for intermediate product storage (5), a detector module (6), a workup module (7), and a system controller (8); b) shows a schematic drawing of an embodiment of the modular continuous flow device comprising three continuous flow modules (1a, 1b, 1c), a reagent supply system (2), a valve assembly (3), a final product collector (31), a mean for controlling flow rates and/or pressure (4) installed between the valve assembly and the final product collector (31), a continuous flow module for intermediate product storage (5), a detector module (6), a workup module (7), and a system controller (8).
Figure 2:
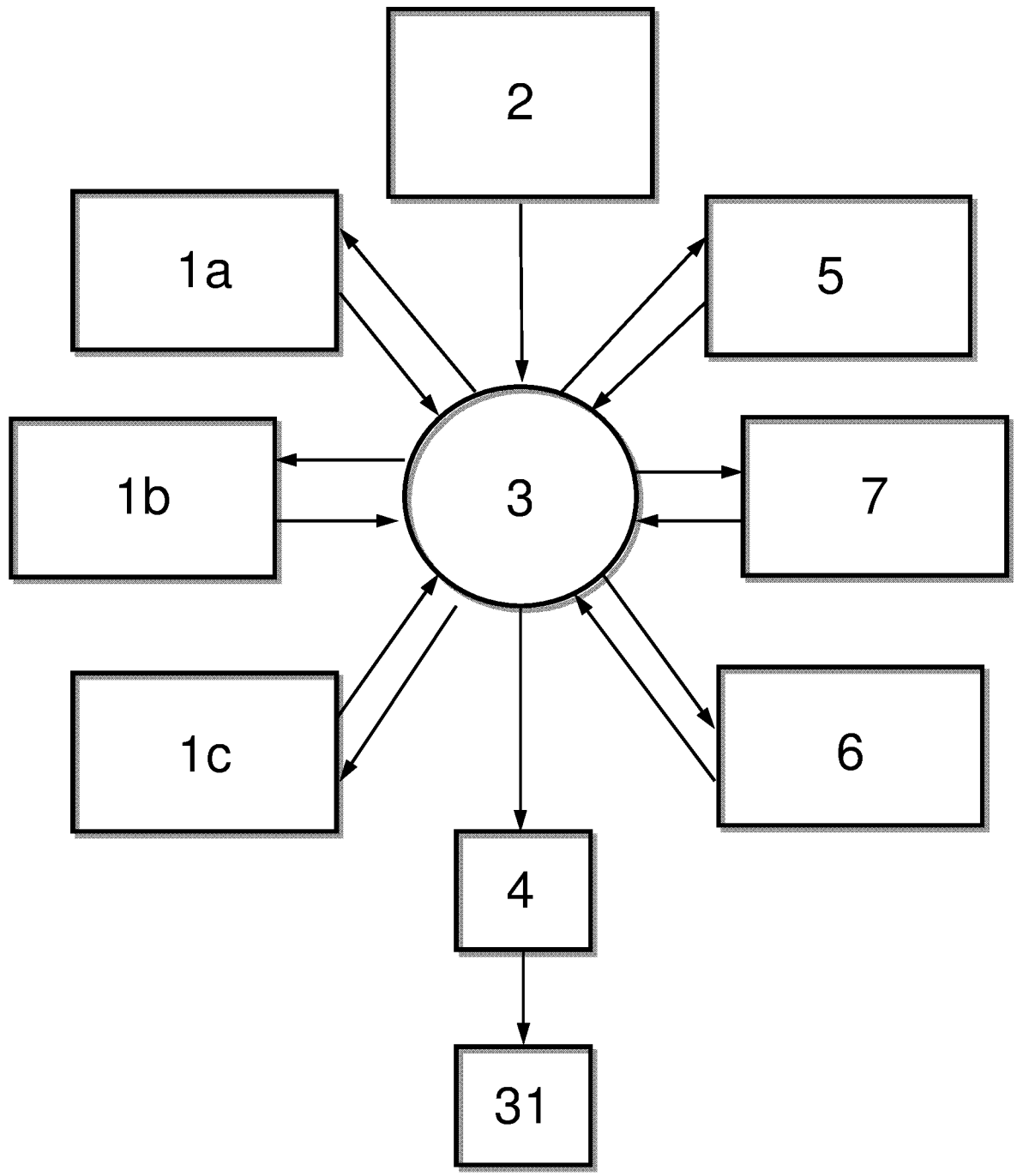
Figure 4:
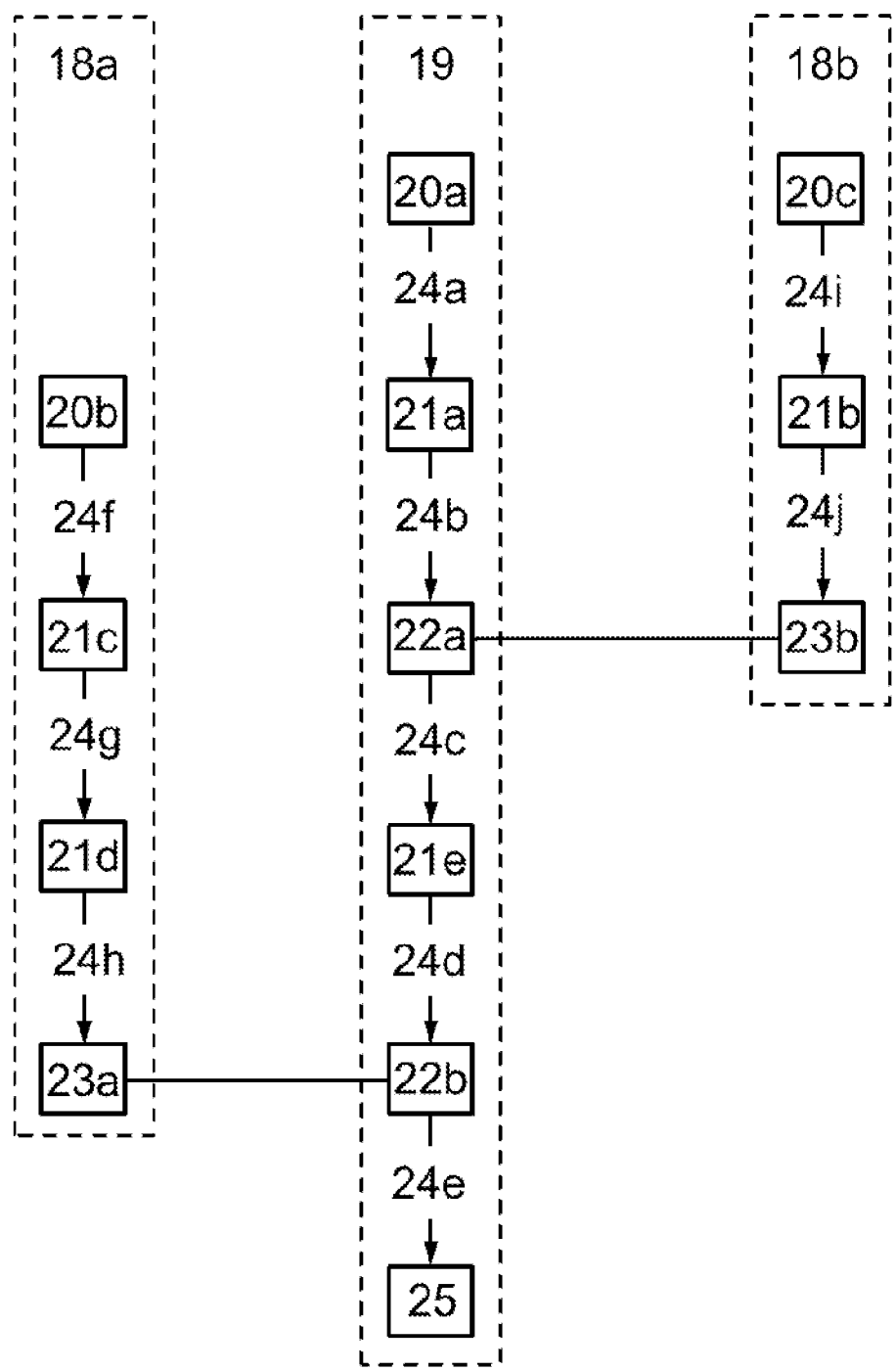
FIG. 4 shows a scheme of a convergent multistep synthesis. The synthesis can be divided into a synthetic main route (19) and in this example two synthetic sub routes (18a, 18b). The synthetic main route (19) is chosen in such a way that it contains the final product (25) and the longest reaction step sequence of reaction steps The synthetic sub routes (18a, 18b) do not lead to the final product (25). Instead the synthetic sub routes (18a,18b) always lead to sub route products (23a,23b).
Figure 5:
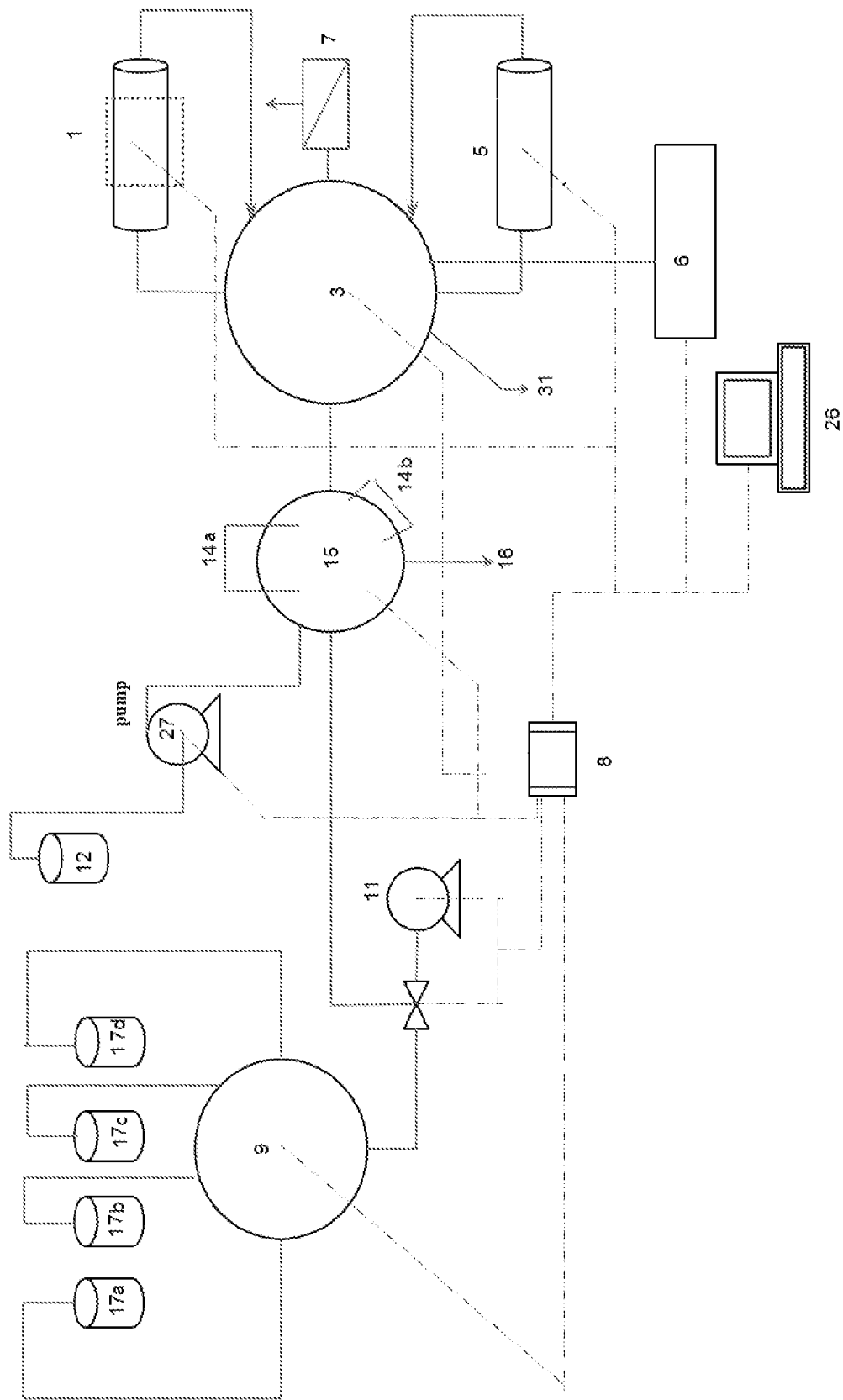
FIG. 5 shows a diagram of a representative example of the modular continuous flow device according to the present invention.

A diagram of the herein described setup is shown in FIG. 5. The inventive modular continuous flow device comprises a reagent supply system (2), a valve assembly (3), mean for controlling flow rates and pressure in form of a pump (27), a plurality of continuous flow modules (1) (depicted in FIG. 5 as one module), a flow reactor for intermediate product storage (5), a workup module (7), a detector module (6), a final product collector (31) and a system controller (8). The reagent supply system is equipped with 4 reagent containers (17a,17b,17c,17d) that are connected to the reagent selector (9). Liquid or dissolved reagents are withdrawn with a syringe pump (11) and are loaded into the respective sample loops (14a, 14b) of the charging station (15). After each loading, the lines are flushed with solvent from the solvent container (12) in order to avoid contamination. Pressure is established by a mean for controlling flow rates and pressure (4) in form of a pump (27). The flow reactor to carry out the reaction is selected with the help of the valve assembly the flow reactors are set to provide the desired reaction conditions, i.e. temperature, pressure, irradiation. Then the reagents are loaded with the help of the charging station (15) into the flow reactor at which the first reaction step takes place. While the first reaction is run, reagents for the second reaction step are loaded from the reagent supply system to the valve assembly and from there to another flow reactor. Both reaction mixtures are afterward directed back to the valve assembly (3) where they are mixed with additional reagents and then submitted to another flow reactor for the third reaction step. Once the reaction is completed, the mixture is then either mixed with additional reagents for various other reactions, or directed to the workup module (7) in form of a liquid-liquid-extraction device, or to a detector module (6) in form of an inline FlowIR detector. When the synthesis is completed the final product is collected in the final product collector (31). The entire synthesis is carried out in an automated way until the desired compounds, with required yields, are obtained. All the components of the device are controlled by dedicated process control software from a computer (26) which is connected to the detector module (6) and the system controller (8), in real time due to the system controller (8).

Example 2: Convergent Synthesis of Rufinamide (28) Using the Inventive Modular Continuous Flow Device (FIG. 6)

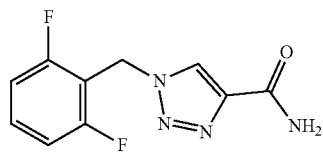 [SMILES: NC(=O)c1cn(Cc2c(F)cccc2F)nn1]

A solution of 2,6-difluorotoluene (128 mg, 1 mmol) and AIBN (azobisisobutyronitrile, 2 mg) in 1 mL ethyl acetate and a solution of NBS (N-bromosuccinimide, 178 mg, 1 mmol) in 1 mL ethyl acetate are prepared and given into their respective reagent container of the reagent supply system. The continuous flow module for heating set to 60° C. Ethyl acetate is flushed through the device. The reagents are then transferred from the reagent supply system to the valve assembly and are then mixed. The valve assembly is set to direct the reagents to the continuous flow module for heating. The mixed reagents enter the continuous flow module for heating. The valve assembly is set to direct the crude difluorobenzyl bromide solution from the continuous flow module for heating to the workup module for washing. The workup module is fed by a saturated aqueous $NaHCO_3$ solution. After liquid-liquid extraction, the difluorobenzyl bromide solution is directed back to the valve assembly where it is mixed with 2.6 mL of a prepared DMSO solution of sodium azide (85 mg, 1.3 mmol) delivered from the reagent supply system. The flow enters then the module for intermediate product storage. At the same time methyl propiolate (126 mg, 1.5 mmol), and a 25% wt. aqueous ammonia solution, which are stored in the reagent supply system are mixed and subjected to the continuous flow module for cooling, which is set to 0° C. beforehand. The mixture resides for 5 minutes in the continuous flow module for cooling before it is directed back to the valve assembly, where it is mixed with the stored intermediate. The combined reagents flow is then directed to the continuous flow module with a packed-bed reactor that is equipped with copper turnings and that is heated to 110° C. After the last reaction step, the flow enters again the valve assembly and is then directed to the outflow behind the back pressure regulator, where the product rufinamide (28) is collected.

Example 3: Multistep Synthesis of N-Fmoc-Protected Pregabalin (29) Using the Inventive Modular Continuous Flow Device (FIG. 7)

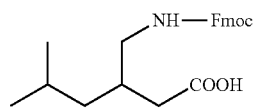

The title compound N-Fmoc-protected pregabalin is synthesized in 7 steps from triethyl phosphonoacetate and isopentanol. The modular continuous flow device for this multistep synthesis comprises besides a valve assembly and a reagent supply system, a continuous flow module for heating, a continuous flow module for cooling, a module for intermediate product storage, a workup module consisting of a liquid-liquid-extraction device capable of multiple extractions, a continuous flow module for gas/liquid reactions and a continuous flow module that comprises a packed-bed reactor. Further each continuous flow module output is equipped with a static inline mixer to reduce dispersion issues.

A solution of triethyl phosphonoacetate (224 mg, 1 mmol) in 1 mL toluene/MeOH (4:1 v/v), a solution of KOtBu (112 mg, 1 mmol) in 1 mL toluene/MeOH and a solution of isopentanol (88 mg, 1 mmol) in 1 mL toluene are prepared and are given into their respective reagent container of the reagent supply system. The reagent supply system contains also a solution of sodium hypochlorite (93 mg, 1.25 mmol) and potassium bromide (12 mg, 0.1 mmol) in 4 mL water. Toluene is flushed through the device. The solutions of triethyl phosphonoacetate and KOtBu are transferred from the reagent supply system to the valve assembly and are combined. The valve assembly is set to direct the reaction mixture to the module for intermediate product storage where the potassium triethyl phosphonoacetate resides for 30 min. In the meantime the continuous flow module for cooling is set to 0° C. and the solutions containing isopentanol and NaOCl are transferred, mixed and directed through the positioned valve assembly to the continuous flow module for cooling. The reaction mixture resides at 0° C. for 25 min and is then passed via the valve assembly to the workup module where the crude isovaleraldehyde solution is washed with saturated aqueous NaHCO$_3$ solution. After phase separation, the isovaleraldehyde solution is directed back to the valve assembly where it is mixed with the stored potassium triethyl phosphonoacetate solution from the continuous flow module for intermediate product storage. The combined reaction mixture is then passed again through the continuous flow module for intermediate product storage in 10 min and afterwards washed with 1 M HCl solution in the workup module. A solution of nitromethane (92 mg, 1.5 mmol) and tetrabutylammonium fluoride (261 mg, 1 mmol) in 1 mL THF is delivered from the reagent supply system and joined together with the ethyl 2-hexenoate. The continuous flow module for heating is heated to 50° C. and the combined reaction mixture is directed to the continuous flow module for heating where it resides for 60 min. Afterwards, the crude reaction mixture is passed via the valve assembly to the workup module, where it is washed with 1 M HCl solution. After phase separation the mixture is combined with a solution of lithium hydroxide (36 mg, 1.5 mmol) in 1 mL water and again directed to the continuous flow module for heating which is still set to 50° C. The combined reagents reside there for 60 min and are then washed with 1 M HCl solution in the workup module. The aqueous phase is extracted with toluene. The toluene extract is combined with the washed reagents flow and then passed via the valve assembly to the continuous flow module for gas-liquid reactions which consists of a tube-in-tube-reactor. The tube-in-tube reactor is saturated with hydrogen gas. Upon passing the mixture through the tube-in-tube reactor the nitrocarboxylic acid stream gets saturated with hydrogen. The hydrogen saturated solution of the nitrocarboxylic acid is then directed to the continuous flow module with Pd/C columns equipped packed-bed reactor. The pregabalin solution is afterwards mixed with a solution of Fmoc-Cl (259 mg, 1 mmol) and N-methylmorpholine (101 mg, 1 mmol) in 2 mL THF provided from the reagent supply system in the valve assembly. Subsequently, the reaction mixture is passed through the module for intermediate product storage for 20 minutes prior washing with saturated aqueous NaHCO$_3$ in the workup module. At last, the N-Fmoc protected pregabalin (29) is collected at the outflow of the device behind the back pressure regulator.

Example 4: Convergent Synthesis of Artemisinin Derivative (30) Using the Inventive Modular Continuous Flow Device (FIG. 8)

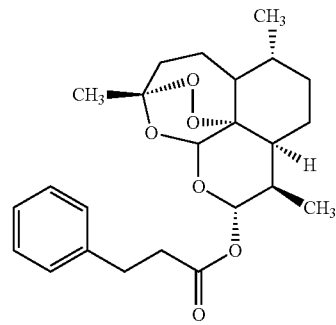 [SMILES: C[C@H]1[C@H](OC(=O)CCc2ccccc2)OC2O[C@]3(C)CCC4[C@H](C)CC[C@@H]1[C@@]24OO3]

A solution of dihydroartemisinic acid (236 mg, 1 mmol), TFA (57 mg, 0.5 mmol) and dicyanoanthracene (1.2 mg, 0.005 mmol) in 2 mL toluene is prepared and is given into the respective reagent container of the reagent supply system. In addition, solutions of phenylpropionic acid (150 mg, 1 mmol) in 1 mL THF, EDC (1-ethyl-3-(3-dimethylaminopropyl)carbodiimide, 155 mg, 1 mmol) in 1 mL THF and N-hydroxysuccinimide (115 mg, 1 mmol) in 1 mL THF are prepared and stored in their respective reagent container of the reagent supply system. These solutions (phenylpropionic acid, EDC and NHS) are withdrawn consecutively from the reagent supply system and mixed together. This reaction mixture is passed through the module for intermediate product storage for 30 minutes. Meanwhile, the continuous flow module for gas-liquid reactions which consists of a tube-in-tube reactor is saturated with oxygen and the valve assembly is set to direct the dihydroartemisinic acid solution injected from the reagent supply system to the tube-in-tube reactor. The dihydroartemisinic acid solution is saturated with oxygen and then passed via the valve assembly to the continuous flow module for photoreactions which consists of a FEP tubing that surrounds a LED module and an electric chiller. The reactor is cooled to −20° C. before the oxygen saturated dihydroartemisinic acid solution is submitted and irradiated for 3 minutes. Afterwards the reaction mixture is directed to the module for intermediate product storage where it resides for 8 minutes at room temperature. Excess oxygen is removed by passing the crude artemisinin solution again through the continuous flow module for gas-liquid reactions which is set to reduced pressure. 0.27 mL of ethanol is then added to the artemisinin solution in the valve assembly before it is directed to the continuous flow module with a packed-bed reactor. The packed-bed reactor is equipped with a column that is packed with a mixture of 650 mg Celite, 650 mg Li$_2$CO$_3$, 650 mg NaBH$_4$ and 520 mg LiCl. The reaction mixture is passed through the column at a flow rate of 0.2 mL/min and is afterwards washed with water in the workup module. The washed dihydroartemisinin solution is then combined and mixed with the stored phenylpropionic acid active ester solution as well as NEt$_3$ (0.1 mL, 0.73 mmol) and is passed to the module for intermediate product storage where it resides for 25 minutes. The crude reaction solution is afterwards washed in the workup module with 1 M HCl solution and the organic phase containing the final product is collected at the outflow of the modular continuous flow device behind the back pressure regulator.

What is claimed is:

1. A modular continuous flow device for multistep synthesis comprising:
    a) a plurality of continuous flow modules (1);
    b) a reagent supply system (2);
    c) a valve assembly (3);
    d) means for controlling flow rates and/or pressure (4);
    wherein each continuous flow module (1) is connected to the valve assembly (3) by at least one inlet and by at least one outlet;
    wherein the continuous flow modules (1) are in a parallel arrangement; and
    wherein the reagent supply system (2) is connected to the valve assembly (3) by one or more inlets and can be connected to at least one continuous flow module (1) by one or more inlets.

2. The modular continuous flow device according to claim 1, wherein the continuous flow modules (1) further comprise at least one flow reactor for intermediate product storage (5).

3. The modular continuous flow device according to claim 1, wherein the continuous flow modules (1) comprise at least one flow reactor for heating, at least one flow reactor for cooling, at least one flow reactor for photochemical reactions, at least one flow reactor for microwave irradiation, at least one flow reactor for electrochemical reactions, at least one flow reactor that is a tube-in-tube reactor, and at least one flow reactor that is a packed-bed reactor.

4. The modular continuous flow device according to claim 1, wherein the continuous flow modules (1) are only connected to each other through the valve assembly (3).

5. The modular continuous flow device according to claim 1, wherein any of continuous flow modules (1) is not directly connected to any other continuous flow module.

6. The modular continuous flow device according to claim 3, wherein the at least one flow reactor for intermediate product storage (5), stores the intermediate product (21) under flow conditions in a closed circuit.

7. The modular continuous flow device according to claim 1, wherein the means for controlling flow rates and/or pressure (4) are adapted to use a different flow rate and/or a different pressure in each continuous flow module (1).

8. The modular continuous flow device according to claim 1 further comprising at least one workup module (7).

9. The modular continuous flow device according to claim 1, wherein the valve assembly (3) consists of at least one multiport switch valve equipped with a mixer and/or equipped with a splitter.

10. The modular continuous flow device according to claim 1, wherein the reagent supply system (2) is connected to an input port of the valve assembly (3) through an injection loop (13) or through a charging station (15).

11. The modular continuous flow device according to claim 1, further comprising mixers installed at the output of each continuous flow module (1) for reducing dispersion effects.

12. The modular continuous flow device according to claim 1, further comprising at least one detector (6) for monitoring the reaction progress, wherein the at least one detector has one input and one output which are connected to the valve assembly (3) over two different fluid connections.

* * * * *